(12) United States Patent
Pryce et al.

(10) Patent No.: US 8,921,789 B2
(45) Date of Patent: Dec. 30, 2014

(54) TUNABLE COMPLIANT OPTICAL METAMATERIAL STRUCTURES

(75) Inventors: Imogen Pryce, Santa Monica, CA (US); Koray Aydin, Skokie, IL (US); Ryan Briggs, Pasadena, CA (US); Harry A. Atwater, South Pasadena, CA (US); Yousif Kelaita, Cupertino, CA (US)

(73) Assignee: California Institute of Technology, Pasadena, CA (US)

( * ) Notice: Subject to any disclaimer, the term of this patent is extended or adjusted under 35 U.S.C. 154(b) by 136 days.

(21) Appl. No.: 13/200,273

(22) Filed: Sep. 21, 2011

(65) Prior Publication Data

US 2012/0154793 A1 Jun. 21, 2012

Related U.S. Application Data

(60) Provisional application No. 61/385,063, filed on Sep. 21, 2010, provisional application No. 61/444,592, filed on Feb. 18, 2011.

(51) Int. Cl.
| | |
|---|---|
| *G01J 5/00* | (2006.01) |
| *G01N 21/65* | (2006.01) |
| *G01N 21/35* | (2014.01) |
| *G01N 21/41* | (2006.01) |

(52) U.S. Cl.
CPC .......... *G01N 21/658* (2013.01); *G01N 21/3581* (2013.01); *G01N 21/3563* (2013.01); *G01N 21/41* (2013.01)
USPC ...................................................... 250/338.1

(58) Field of Classification Search
CPC ........................................................ G01J 5/00
USPC ...................................................... 250/338.1
See application file for complete search history.

(56) References Cited

U.S. PATENT DOCUMENTS

| | | | |
|---|---|---|---|
| 2009/0310902 A1* | 12/2009 | Smith et al. ..................... | 385/12 |
| 2012/0057616 A1* | 3/2012 | Padilla et al. .................. | 374/179 |
| 2012/0181896 A1* | 7/2012 | Kornbluh et al. ............. | 310/300 |

OTHER PUBLICATIONS

Amstad, Esther, et al., "Triggered Release from Liposomes through Magnetic Actuation of Iron Oxide Nanoparticle Containing Membranes", *Nano Letters*, 2011, vol. 11, pp. 1664-1670.
Aydin, Koray, et al., "Symmetry Breaking and Strong Coupling in Planar Optical Metamaterials", *Optics Express*, 2010, vol. 18, No. 13, pp. 13407-13417.
Bukasov, Rostislav, et al., "Silver Nanocrescents with Infrared Plasmonic Properties as Tunable Substrates for Surface Enhanced Infrared Absorption Spectroscopy", 2009, *Analytical Chemistry*, vol. 81, No. 11, pp. 4531-4535.

(Continued)

*Primary Examiner* — Constantine Hannaher
*Assistant Examiner* — Hugh H Maupin
(74) *Attorney, Agent, or Firm* — Christine, Parker & Hale, LLP

(57) ABSTRACT

A tunable metamaterial structure, comprises a flexible substrate capable of being strained, a metamaterial pattern on a surface of the flexible substrate, and a metal layer on the metamaterial pattern. The flexible substrate of the tunable metamaterial structure is a strained and relaxed substrate which has been strained to a degree sufficient to register a resonant response upon relaxation that is shifted relative to the resonant response of the flexible substrate prior to being strained. The application of strain to the flexible substrate of the metamaterial structure enables tuning of the resonant frequency.

19 Claims, 17 Drawing Sheets
(17 of 17 Drawing Sheet(s) Filed in Color)

(56) References Cited

OTHER PUBLICATIONS

Bukasov, Rostislav, et al., "Probing the Plasmonic Near-Field of Gold Nanocrescent Antennas", *ACS Nano*, 2010, vol. 4, No. 11, pp. 6639-6650.

Chen, Hou-Tong, et al., "Active Terahertz Metamaterial Devices", *Nature*, 2006, vol. 444, pp. 597-600.

Chen, Hou-Tong, et al., "Experimental Demonstration of Frequency-Agile Terahertz Metamaterials", *Nature Photonics*, 2008, vol. 2, pp. 295-298.

Cole, Robin M., et al., "Stretchable Metal-Elastomer Nanovoids for Tunable Plasmons," *Applied Physics Letters*, 2009, vol. 95, pp. 154103-1 to 154103-3.

Cubukcu, Ertugrul, et al., "Split Ring Resonator Sensors for Infrared Detection of Single Molecular Monolayers", *Applied Physics Letters*, 2009, vol. 95, pp. 043113-1 to 043113-4.

Dicken, Matthew J., et al., "Frequency Tunable Near-Infrared Metamaterials Based on $VO_2$ Phase Transition", *Optics Express*, 2009, vol. 17, No. 20, pp. 18330-18339.

Dolling, G., et al., "Cut-Wire Pairs and Plate Pairs as Magnetic Atoms for Optical Metamaterials", *Optics Letters*, 2005, vol. 30, No. 23, pp. 3198-3200.

Dong, Zheng-Gao, et al., "Enhanced Sensing Performance by the Plasmonic Analog of Electromagnetically Induced Transparency in Active Metamaterials", *Applied Physics Letters*, 2010, vol. 97, pp. 114101-1 to 114101-3; doi:10.1063/1.3488020.

Fan, Jonathan A., et al., "Self-Assembled Plasmonic Nanoparticle Clusters," *Science*, 2010, vol. 328, pp. 1135-1138.

Fedotov, V. A., et al., "Sharp Trapped-Mode Resonances in Planar Metamaterials with a Broken Structural Symmetry", *Physical Review Letters*, 2007, vol. 99, pp. 147401-1 to 147401-4.

Gansel, Justyna K., et al., "Gold Helix Photonic Metamaterial as Broadband Circular Polarizer", *Science*, 2009, vol. 325, pp. 1513-1515.

Hao, Feng, et al., "Tunability of Subradiant Dipolar and Fano-Type Plasmon Resonances in Metallic Ring/Disk Cavities: Implications for Nanoscale Optical Sensing", *ASC Nano*, 2009, vol. 3, No. 3, pp. 643-652.

Hao, Feng, et al., "Symmetry Breaking in Plasmonic Nanocavities: Subradiant LSPR Sensing and a Tunable Fano Resonance", *Nano Letters*, 2008, vol. 8, No. 11, pp. 3983-3988.

Huang, Fumin, et al., "Actively Tuned Plasmons on Elastomerically Driven Au Nanoparticle Dimers", *Nano Letters*, 2010, vol. 10, pp. 1787-1792.

Jensen, T. R., et al., "Surface-Enhanced Infrared Spectroscopy: A Comparison of Metal Island Films with Discrete and Nondiscrete Surface Plasmons", *Applied Spectroscopy*, 2000, vol. 54, No. 3, pp. 371-377.

Klar, T., et al., "Surface-Plasmon Resonances in Single Metallic Nanoparticles", *Physical Review Letters*, 1998, vol. 80, No. 19, pp. 4249-4252.

Kneipp, Katrin, et al., Single Molecule Detection Using Surface-Enhanced Raman Scattering (SERS), *Physical Review Letters*, 1997, vol. 78, No. 9, pp. 1667-1670.

Kottman, J. P., et al., "Non-regularly Shaped Plasmon Resonant Nanoparticle as Localized Light Source for Near-Field Microscopy", *Journal of Microscopy*, 2001, vol. 202, pt. 1, pp. 60-65.

Kubo, Wakana, et al., "Au Double Nanopillars with Nanogap for Plasmonic Sensor", *Nano Letters*, 2011, vol. 11, pp. 8-15.

Kumar, Amit, et al., "Features of Gold Having Micrometer to Centimeter Dimensions Can be Formed Through a Combination of Stamping with an Elastomeric Stamp and an Alkanethiol 'Ink' Following by Chemical Etching", *Applied Physics Letters*, 1993, vol. 63, No. 14, pp. 2002-2004.

Kundu, Janardan, et al., "Surface Enhanced Infrared Absorption (SEIRA) Spectroscopy on Nanoshell Aggregate Substrates", *Chemical Physics Letters*, 2008, vol. 452, pp. 115-119.

Lal, Surbhi, et al., "Tailoring Plasmonic Substrates for Surface Enhanced Spectroscopies", *Chemical Society Review*, 2008, vol. 37, pp. 898-911.

Le, Fei, et al., "Metallic Nanoparticle Arrays: A Common Substrate for Both Surface-Enhanced Raman Scattering and Surface-Enhanced Infrared Absorption", *ASC Nano*, 2008, vol. 2, No. 4, pp. 707-718.

Linden, Stefan, et al., "Magnetic Response of Metamaterials at 100 Terahertz", *Science*, 2004, vol. 306, pp. 1351-1353.

Liu, Jianping, et al., "In Situ Microarray Fabrication and Analysis Using a Microfluidic Flow Cell Array Integrated with Surface Plasmon Resonance Microscopy", *Analytical Chemistry*, 2009, vol. 81, No. 11, pp. 4296-4301.

Liu, Na, et al., "Electromagnetic Resonances in Single and Double Split-Ring Resonator Metamaterials in the Near Infrared Spectral Region", *Phys. Status Solidi (b)*, 2007, vol. 244, No. 4, pp. 1251-1255.

Liu, Zhengtong, et al., "Translation of Nanoantenna Hot Spots by a Metal-Dielectric Composite Superlens", *Applied Physics Letters*, 2009, vol. 95, pp. 033114-1 to 033114-3.

Liu, Na, et al., "Plasmonic Analogue of Electromagnetically Induced Transparency at the Drude Damping Limit", *Nature Materials*, 2009, vol. 8, pp. 758-762.

Liu, Na, et al., "Planar Metamaterial Analogue of Electromagnetically Induced Transparency for Plasmonic Sensing", *Nano Letters*, 2010, vol. 10, pp. 1103-1107.

McFarland, Adam D., et al., "Single Silver Nanoparticles as Real-Time Optical Sensors with Zeptomole Sensitivity", *Nano Letters*, 2003, vol. 3, No. 8, pp. 1057-1062.

Melik, Rohat, et al., "Metamaterial-Based Wireless Strain Sensors", *Applied Physics Letters*, 2009, vol. 95, pp. 011106-1 to 011106-3.

Mohri, Nobuyuki, et al., "Desorption of 4-Aminobenzenethiol Bound to a Gold Surface", *Langmuir*, 1998, vol. 14, pp. 2343-2347.

Nehl, Colleen, L., et al., "Optical Properties of Star-Shaped Gold Nanoparticles", *Nano Letters*, 2006, vol. 6, No. 4, pp. 683-688.

Neubrech, Frank, et al., Resonant Plasmonic and Vibrational Coupling in a Tailored Nanoantenna for Infrared Detection, *Physical Review Letters*, 2008, vol. 101, pp. 157403-1 to 157403-4.

Nie, Shuming, et al., "Probing Single Molecules and Single Nanoparticles by Surface-Enhanced Raman Scattering", *Science, New Series*, 1997, vol. 275, No. 5303, pp. 1102-1106.

Olcum, Selim, et al., "Tunable Surface Plasmon Resonance on an Elastomeric Substrate", *Optics Express*, 2009, vol. 17, No. 10, pp. 8542-8547.

Osawsa, Masatoshi, et al., "Surface-Enhanced Infrared Spectroscopy: The Origin of the Absorption Enhancement and Band Selection Rule in the Infrared Spectra of Molecules Adsorbed on Fine Metal Particles", *Applied Spectroscopy*, 1993, vol. 47, No. 9, pp. 1497-1502.

Pryce, Imogen M., et al., "Highly Strained Compliant Optical Metamaterials with Large Frequency Tunability", *Nano Letters*, 2010, vol. 10, pp. 4222-4227.

Rogacheva, A.V., et al., "Giant Gyrotropy Due to Electromagnetic-Field Coupling in a Bilayered Chiral Structure", *Physical Review Letters*, 2006, vol. 97, pp. 177401-1 to 177401-4.

Sherry, Lief J., et al., "Localized Surface Plasmon Resonance Spectroscopy of Single Silver Triangular Nanoprisms", *Nano Letters*, 2006, vol. 6, No. 9, pp. 2060-2065.

Rogers, John A., et al., "Materials and Mechanics for Stretchable Electronics", *Science*, 2010, vol. 327, pp. 1603-1607.

Samson, Z. L., et al., "Metamaterial Electro-Optic Switch of Nanoscale Thickness", *Applied Physics Letters*, 2010, vol. 96, pp. 143105-1 to 143105-3.

Sersic, Ivana, et al., "Electric and Magnetic Dipole Coupling in Near-Infrared Split-Ring Metamaterial Arrays", *Physical Review Letters*, 2009, vol. 103, pp. 213902-1 to 213902-4.

Shalaev, Vladimir M., "Optical Negative-Index Metamaterials", *Nature Photonics*, 2007, vol. 1, pp. 41-48.

Smith, A. Lee, et al., Vibrational Spectra of $Me_2SiCl_2$, $Me_3SiCl$, $Me_3SiOSiMe_3$, $(Me_2SiO)_3$, $(Me_2SiO)_4$, $(Me_2SiO)_x$, and Their Deuterated Analogs, *Applied Spectroscopy*, 1984, vol. 38, No. 6, pp. 822-834.

Smith, D. R., et al., "Metamaterials and Negative Refractive Index", *Science*, 2004, vol. 305, pp. 788-792.

Tam, Felicia, et al., "Geometrical Parameters Controlling Sensitivity of Nanoshell Plasmon Resonances to Changes in Dielectric Environment", *J. Phys. Chem. B*, 2004, vol. 108, No. 45, pp. 17290-17294.

(56) References Cited

OTHER PUBLICATIONS

Tao, Hu, et al., "Highly Flexible Wide Angle of Incidence Terahertz Metamaterial Absorber: Design, Fabrication and Characterization", *Physical Review B*, 2008, vol. 78, pp. 241103-1 to 241103-4.

Tao, Hu, et al., "Terahertz Metamaterials on Free-Standing Highly-Flexible Polymide Substrates", Journal of Physics D: *Applied Physics*, 2008, vol. 41, pp. 1-5.

Tao, Hu, et al., "Recorifigurable Terahertz Metamaterials", *Physical Review Letters*, 2009, vol. 103, pp. 147401-1 to 147401-4.

Underwood, Sylvia, et al., "Effect of the Solution Refractive Index on the Color of Gold Colloids", *Langmuir*, 1994, vol. 10, pp. 3427-3430.

Verellen, Niels, et al., "Fano Resonances in Individual Coherent Plasmonic Nanocavities", *Nano Letters*, 2009, vol. 9, No. 4, pp. 1663-1667.

Wang, Hui, et al., "Plasmonic Nanoshell Arrays Combine Surface-Enhanced Vibrational Spectroscopies on a Single Substrate", *Angewandte Chemie Int. Ed.*, 2007, vol. 46, pp. 9040-9044.

Xu, Hongxing, et al., "Spectroscopy of Single Hemoglobin Molecules by Surface Enhanced Raman Scattering", *Physical Review Letters*, 1999, vol. 83, No. 21, pp. 4357-4360.

Zhang, Shuang, et al., "Plasmon-Induced Transparency in Metamaterials", *Physical Review Letters*, 2008, vol. 101, pp. 047401-1 to 047401-4.

\* cited by examiner

FIG. 2a
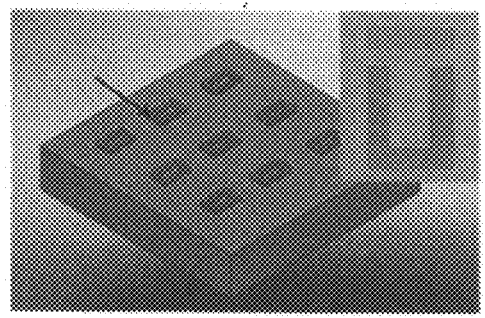
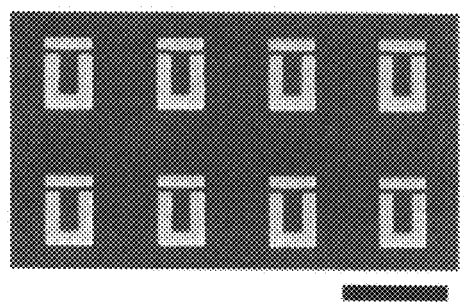
FIG. 2b
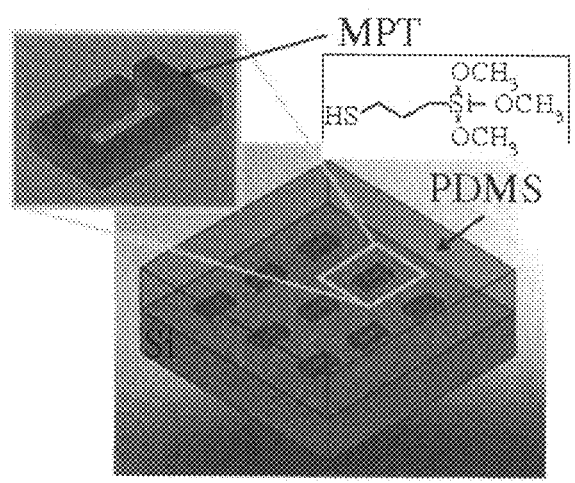

FIG. 3a
FIG. 3b
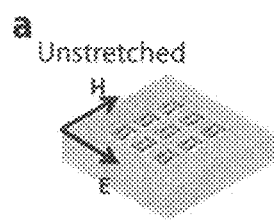
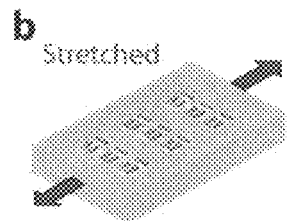
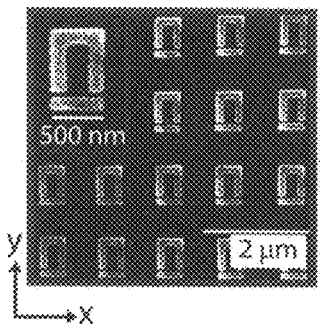
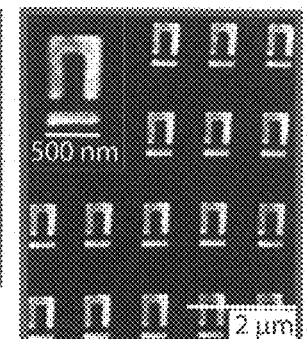
FIG. 3c
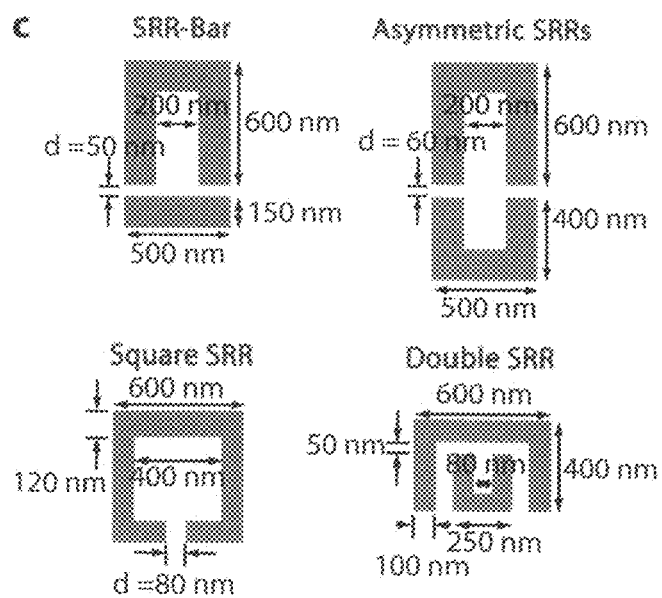

FIG. 4a
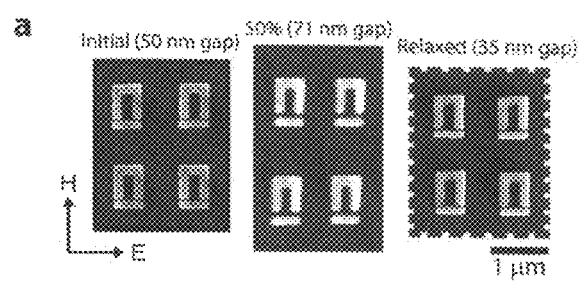
FIG. 4c
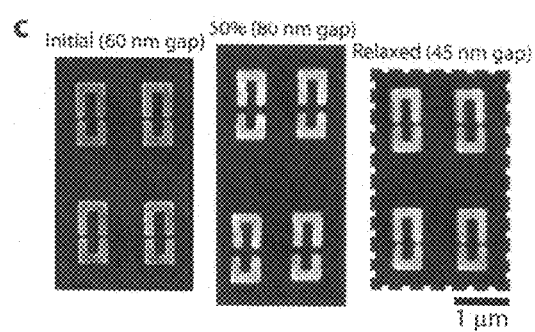
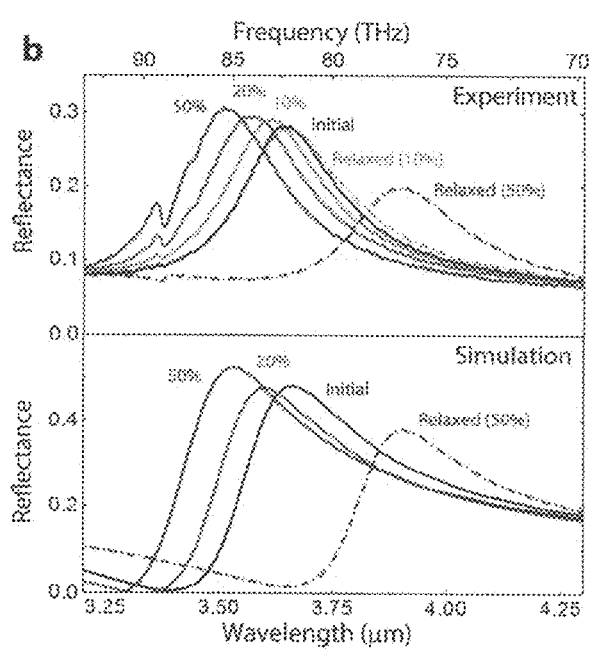
FIG. 4b
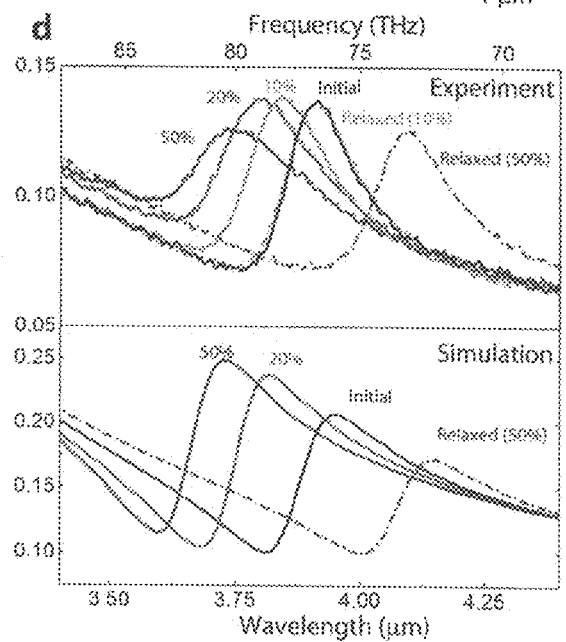
FIG. 4d

FIG. 5a
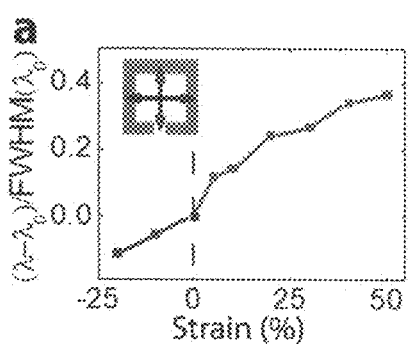
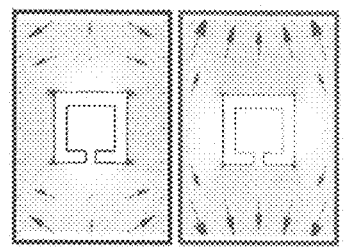
FIG. 5b
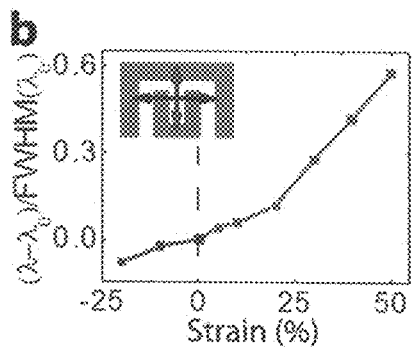
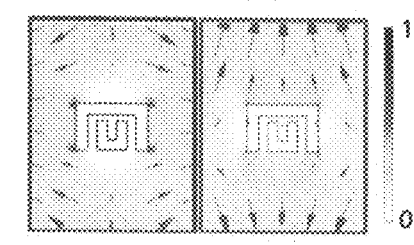
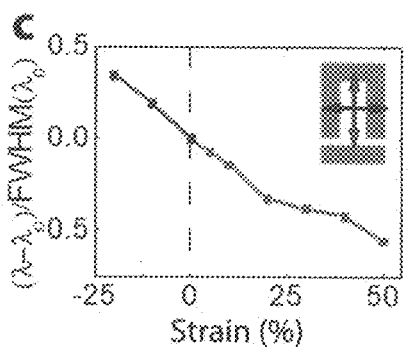
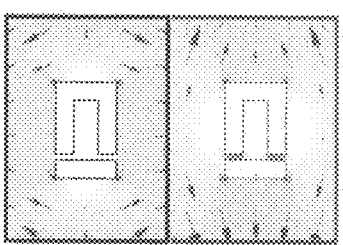
FIG. 5c
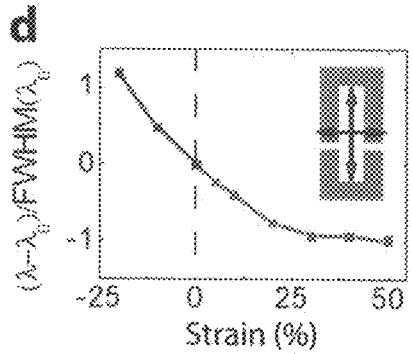
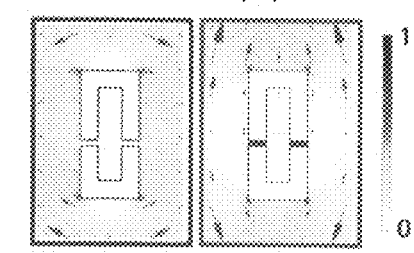
FIG. 5d FIG. 7a(i)  FIG. 7a(ii)  FIG. 7a(iii)
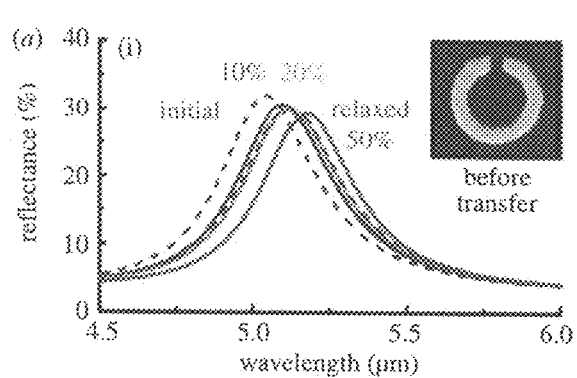 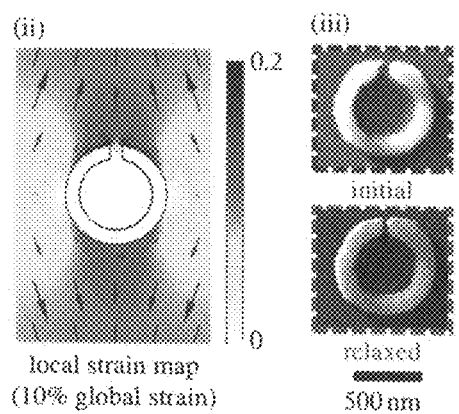 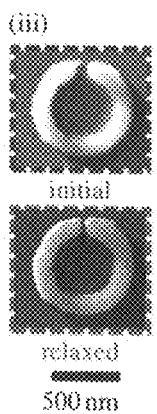
FIG. 7b(i)  FIG. 7b(ii)  FIG. 7b(iii)
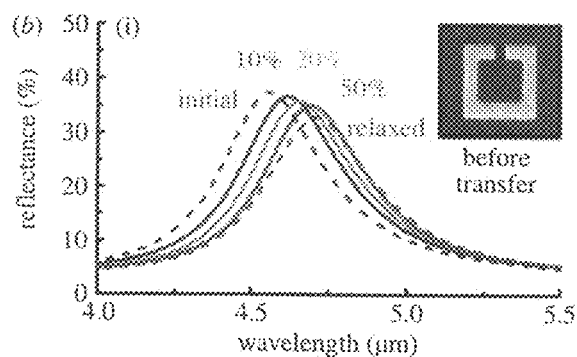 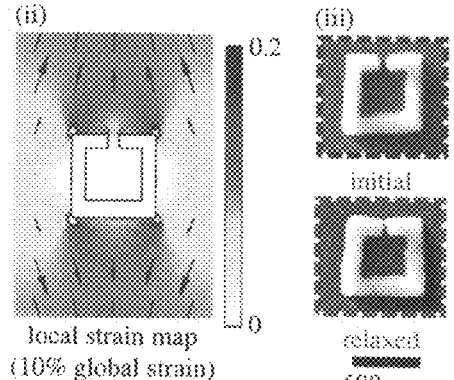 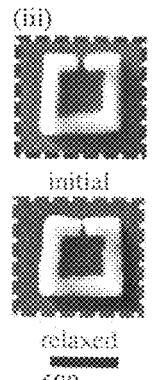

$|E_x|^2$ ($\lambda = 3.37$ μm)

FIG. 10a
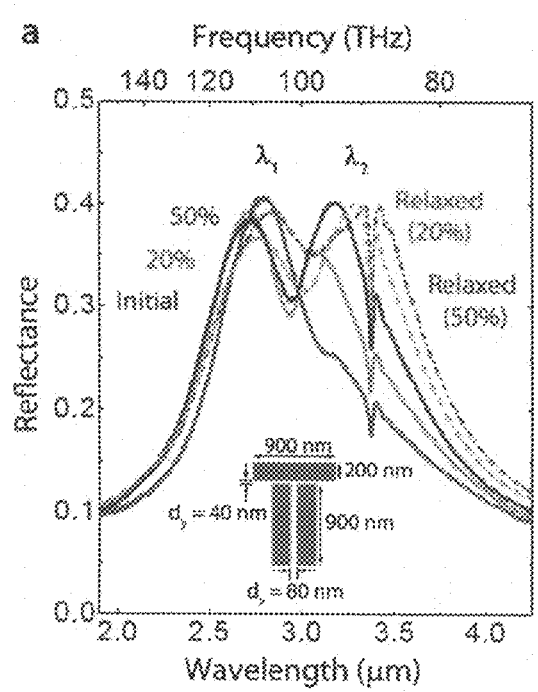
FIG. 10b
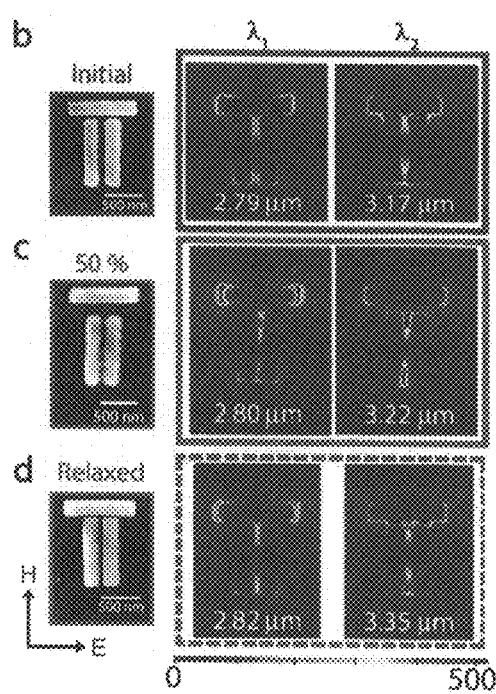
FIG. 10c
FIG. 10d

FIG. 13A   FIG. 13B   FIG. 13C
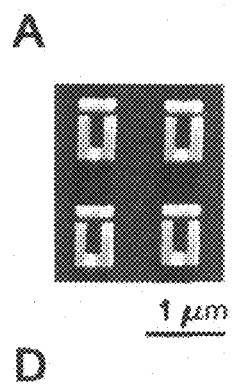
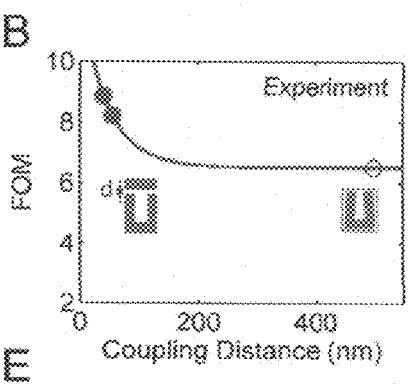
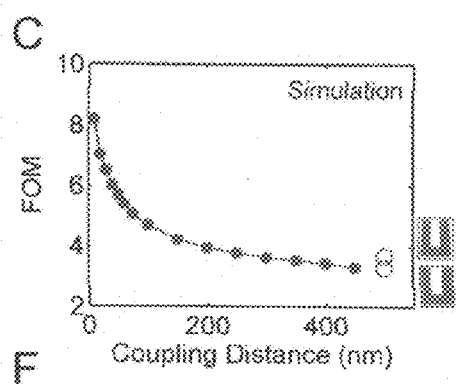
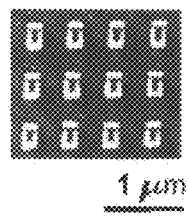
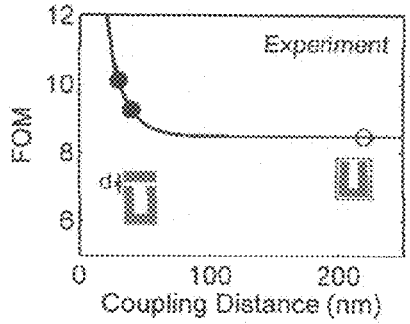
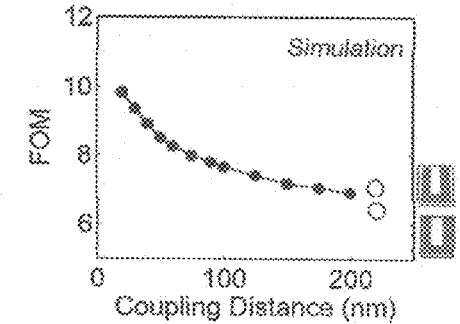
FIG. 13D   FIG. 13E   FIG. 13F

FIG. 14A
FIG. 14B
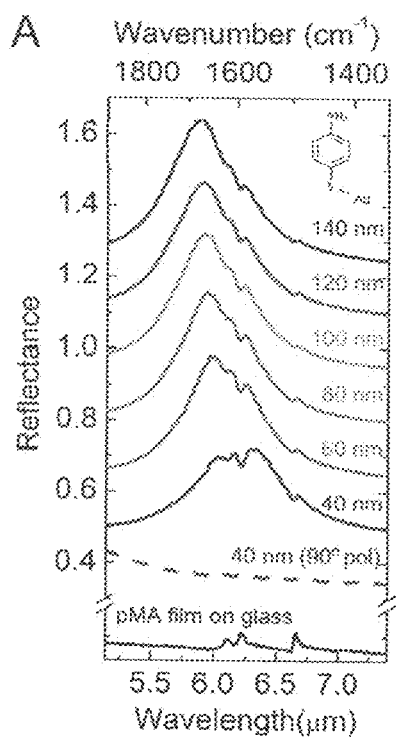
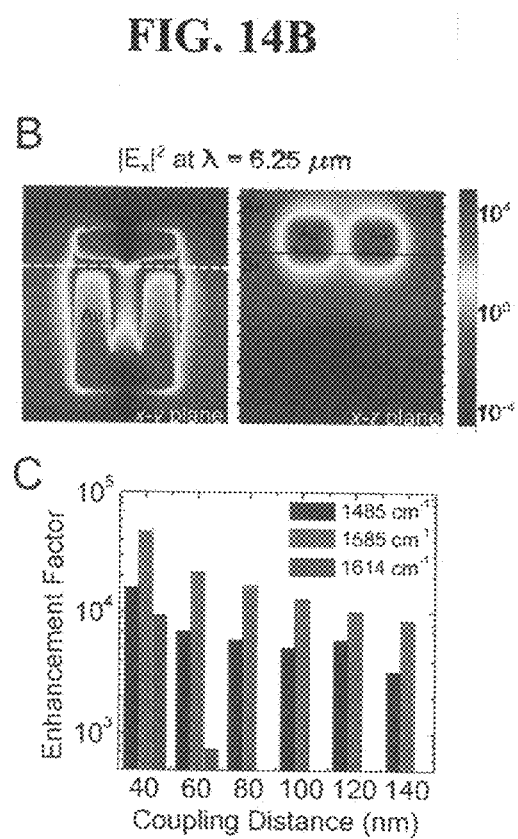
FIG. 14C

TUNABLE COMPLIANT OPTICAL METAMATERIAL STRUCTURES

CROSS-REFERENCE TO RELATED APPLICATIONS(S)

This application claims priority to and the benefit of U.S. Provisional Application Ser. No. 61/385,063, filed Sep. 21, 2010 and entitled COMPLIANT OPTICAL METAMATERIALS, the entire content of which is incorporated herein by reference, and to U.S. Provisional Application Ser. No. 61/444,592, filed Feb. 18, 2011 and entitled HIGHLY COMPLIANT METAMATERIALS FOR RESONANTLY ENHANCED INFRARED ABSORPTION AND REFRACTIVE INDEX SENSING.

STATEMENT REGARDING FEDERALLY SPONSORED RESEARCH OR DEVELOPMENT

The invention described herein was made in the performance of work under Grant No. FA9550-09-1-0673 awarded by the Air Force (AFOSR) and Grant No. W911NF-07-1-0410 awarded by the U.S. Army Robert Morris (ARO), and is subject to the provisions of Public Law 96-517 (35 U.S.C. §202) in which the Contractor has elected to retain title.

TECHNICAL FIELD

The invention is directed to strained compliant optical metamaterials having large frequency tunability.

BACKGROUND

Metamaterials are artificially engineered composites that can exhibit optical responses unattainable in their component materials. Indeed, electromagnetic metamaterials are composites engineered at the subwavelength scale to have specific optical properties. Behavior that is unattainable in any of the constituent materials can be demonstrated by carefully designing individual unit cells. The optical response of a metamaterial can be engineered by manipulation of the size, pattern, and composition of its subwavelength unit cells. This response, however, is usually fixed at the time of fabrication yielding materials that are essentially "passive" and operate over a limited bandwidth. The response of otherwise passive metamaterials can be rendered active by integrating dynamic components into the design. Active metamaterials control the resonant response of a material by incorporating dynamic components at the unit cell or substrate level. These active metamaterials, which seek to tune the resonant frequency range via control of the active medium, represent a new class of designs.

Introducing tunability by controllably activating a metamaterial system is important for the development of a number of devices including modulators, tunable filters and concentrators. Several approaches, ranging from electrical probing of single unit cells to thermal actuation, have been used to demonstrate amplitude modulation and frequency tuning of the resonant response. To date, amplitude modulation of optical metamaterials, which affects the intensity of the response at the resonant wavelength, has been achieved via electrical carrier injection in semiconductor substrates and mechanical reorientation of resonant elements using microelectromechanical systems. Frequency tunability has also been demonstrated by changing the dielectric environment of the resonator with phase-transition materials, liquid crystals, and optical pumping of the substrate.

SUMMARY

Embodiments of the present invention are directed to a tunable metamaterial structure, comprising a flexible substrate capable of being strained, a metamaterial pattern on a surface of the flexible substrate, and a metal layer on the metamaterial pattern. The flexible substrate of the structure is a strained and relaxed substrate which has been strained to a degree sufficient to register a resonant response upon relaxation that is shifted relative to a resonant response of the flexible substrate prior to being strained. In some embodiments, depending on the material of the flexible substrate and the pattern of the metamaterial, the strained and relaxed substrate has been strained to a degree of about 5% or greater. In other embodiments, the strained and relaxed substrate has been strained to a degree of about 10% or greater. In still other embodiments, the strained and relaxed substrate has been strained to a degree of about 20% or greater. In some exemplary embodiments, the strained and relaxed substrate has been strained to a degree of up to about 100%. In still other embodiments, the strained and relaxed substrate has been strained to a degree of about 5% to about 50%. In yet other embodiments, the strained and relaxed substrate has been strained to a degree of about 10% to about 50%. In other exemplary embodiments, the strained and relaxed substrate has been strained to a degree of about 20% to about 50%.

The flexible substrate of the metamaterial structure includes a material capable of being subjected to the required amount of strain without suffering significant distortion. In some embodiments, for example, the material of the flexible substrate is selected from flexible polymers, rubbers and vinyl acetates. In some exemplary embodiments, the material of the flexible substrate is selected from polydimethylsiloxane (PDMS), polyimide, polybutadiene rubbers, and vinyl acetates. In still other embodiments, the material of the flexible substrate is polydimethylsiloxane (PDMS).

In some embodiments, the tunable metamaterial structures are used for resonantly enhanced infrared spectroscopy or refractive index sensing. Accordingly, in some embodiments, the metamaterial structure is used to sense an analyte. In these embodiments, the metamaterials can function as an infrared absorption signal enhancer that enhances the signal of the analyte which is adsorbed on a surface of the flexible substrate and the metal layer. One exemplary analyte is p-mercaptoaniline.

The metal of the metal layer may be any suitable metal. In some embodiments, for example, the metal is selected from Au, Ag, Cu and Pt.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 2a depicts the first step in a sequence for fabricating compliant metamaterials according to embodiments of the present invention, in which the SRRs are lithographically patterned on a Si handle wafer. The scanning electron micrograph shows the resonators as patterned on Si.

FIG. 2b is the second step in the sequence of FIG. 2a, in which Au is functionalized with MPT and embedded in PDMS.

Figure 2C:
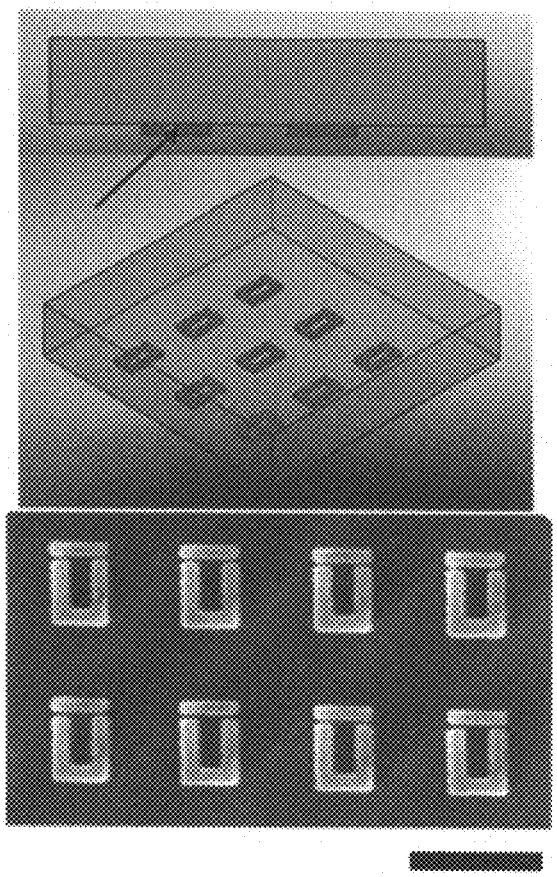

FIG. 2c is the third step in the sequence of FIG. 2a, in which Si wafer is back-etched via RIE to leave a free-standing PDMS substrate. The SEM shows the fidelity of the pattern transfer.

FIG. 3a is a schematic of a metamaterial structure with Au split ring resonators prior to stretching according to embodiments of the present invention. The polarization of the incident electromagnetic radiation is also indicated. The SEM image is of a unit cell and representative array prior to stretching.

FIG. 3b is a schematic of a stretched array according to embodiments of the present invention. The bottom panel includes ESEM images corresponding to 50% strain of the array of FIG. 3a.

FIG. 3c depicts schematics of SRR-bar, asymmetric SRRs, square SRRs and double SRR unit cell structures with their dimensions.

FIG. 4a depicts ESEM images of an array of 2×2 SRR-bar unit cells initially, relaxed, and for 50% strain. The measured gap distances from the ESEM images are shown in parentheses.

FIG. 4b depicts in the top panel the experimental FTIR reflectance data for an array of SRR-bar structures under applied strains of up to 50%, and in the bottom panel the corresponding simulated reflectance data.

FIG. 4c depicts ESEM images of an array of 2×2 ACSRR unit cells initially, relaxed, and for 50% strain. The measured gap distances from the ESEM images are shown in parentheses.

FIG. 4d depicts in the top panel the experimental FTIR reflectance data for an array of ACSRR structures under applied strains of up to 50%, and in the bottom panel the corresponding simulated reflectance data.

FIG. 5a in the top panel shows the reflection peak position shift divided by the FWHM of the initial reflection peak for square SRR arrays stretched along the primary strain axis (positive tensile strain, shown in red) and the secondary strain axis (negative compressive strain, shown in blue). In the bottom panel is shown the strain density map for perturbations along the primary (red outline) or secondary (blue outline) strain axis. These data are normalized to the maximum for the SRR-bar configuration.

FIG. 5b in the top panel shows the reflection peak position shift divided by the FWHM of the initial reflection peak for double SRR arrays stretched along the primary strain axis (positive tensile strain, shown in red) and the secondary strain axis (negative compressive strain, shown in blue). In the bottom panel is shown the strain density map for perturbations along the primary (red outline) or secondary (blue outline) strain axis. These data are normalized to the maximum for the SRR-bar configuration.

FIG. 5c in the top panel shows the reflection peak position shift divided by the FWHM of the initial reflection peak for SRR-bar arrays stretched along the primary strain axis (positive tensile strain, shown in red) and the secondary strain axis (negative compressive strain, shown in blue). In the bottom panel is shown the strain density map for perturbations along the primary (red outline) or secondary (blue outline) strain axis.

FIG. 5d in the top panel shows the reflection peak position shift divided by the FWHM of the initial reflection peak for asymmetric coupled SRR arrays stretched along the primary strain axis (positive tensile strain, shown in red) and the secondary strain axis (negative compressive strain, shown in blue). In the bottom panel is shown the strain density map for perturbations along the primary (red outline) or secondary (blue outline) strain axis. These data are normalized to the maximum for the SRR-bar configuration.

Figure 6:
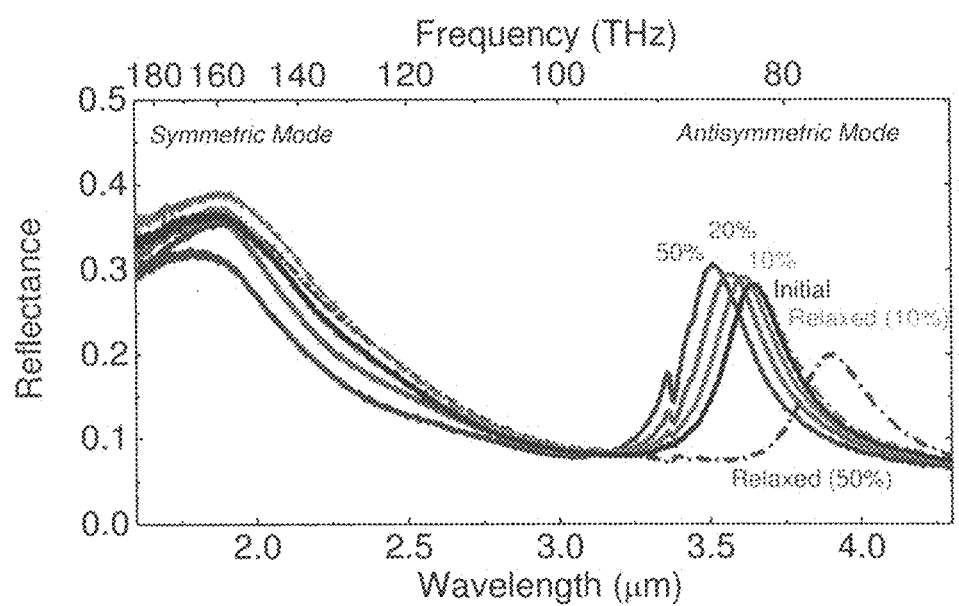

FIG. 6 depicts the reflectance data for the SRR-bar coupled resonator array. These are the same data as in FIG. 4b, but here the reported wavelength range is extended to shorter wavelengths in order to show both the symmetric and antisymmetric resonant modes.

FIG. 7a(i) depicts the FTIR spectra for a circular SRR (CSRR) for strains of up to 50%. The inset shows the resonator on Si prior to transfer to the PDMS.

FIG. 7a(ii) shows the local strain map for a CSRR as calculated using FEM modeling. The color map corresponds to the local strain induced in the resonator, while the arrows indicate the local displacement.

FIG. 7a(iii) depicts environmental SEM (ESEM) images of a single resonator (CSRR) after transfer ("initial") and after mechanical deformation ("relaxed").

FIG. 7b(i) depicts the FTIR spectra for a square SRR (sqSRR) for strains of up to 50%. The inset shows the resonator on Si prior to transfer to the PDMS.

FIG. 7b(ii) shows the local strain map for a sqSRR as calculated using FEM modeling. The color map corresponds to the local strain induced in the resonator, while the arrows indicate the local displacement.

FIG. 7b(iii) depicts environmental SEM (ESEM) images of a single resonator (sqSRR) after transfer ("initial") and after mechanical deformation ("relaxed").

Figure 8A:
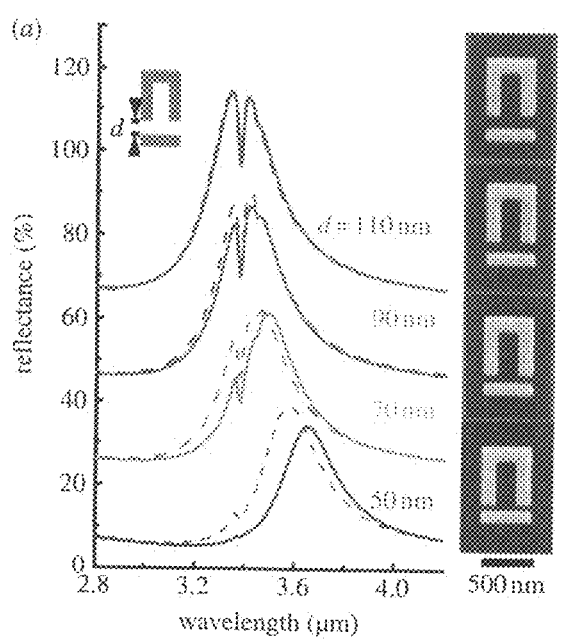

FIG. 8a depicts the FTIR spectra for various SRR-nanowire-coupled resonator pair arrays. The spacing d is varied from d=110 nm to d=50 nm. Each dashed line shows how 5% global strain affects the resonant peak position. The SEM images to the right of the FTIR data show the SRR-bar designs on Si prior to transferring to PDMS.

Figure 8B:
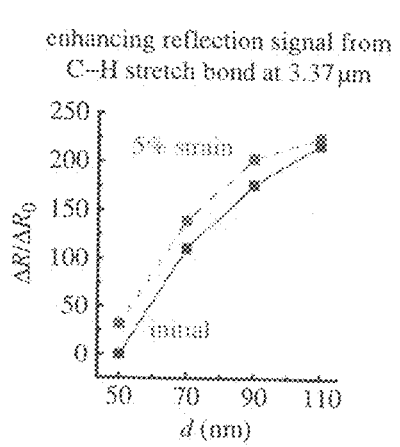

FIG. 8b depicts the change in reflection for the absorption feature corresponding to the vibrational mode of the C—H stretch bond in PDMS. The change is reported relative to the reflection dip for bare PDMS. The data for both the initial position (solid line) and the 5 strain (dashed line) resonant peak position are reported.

Figure 9A:
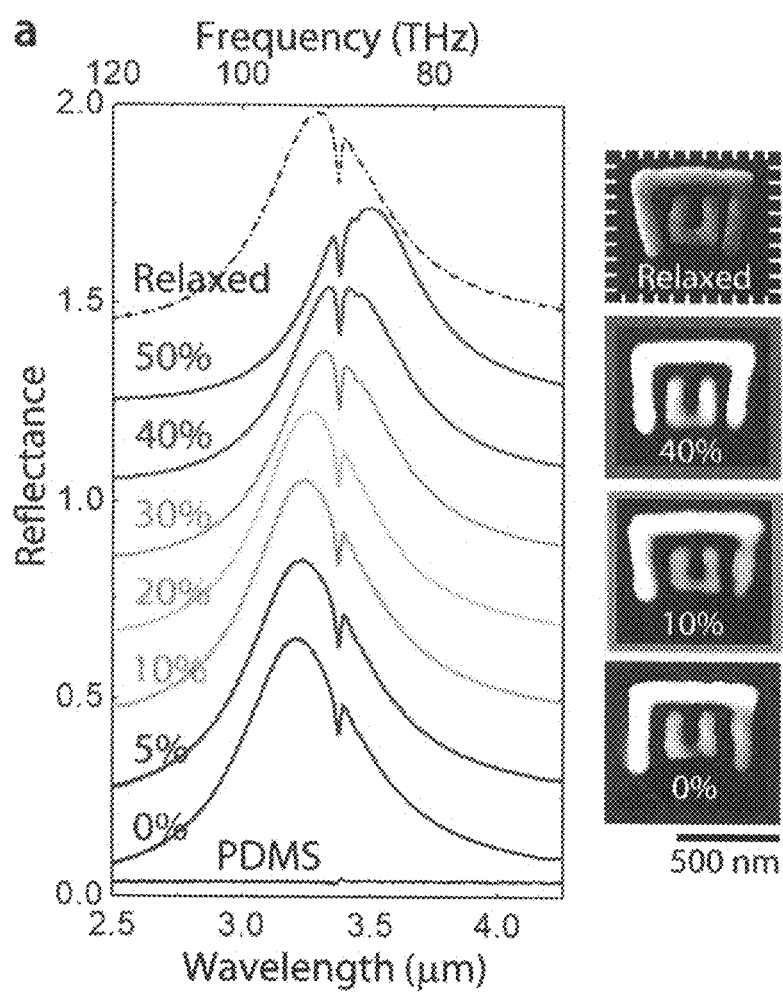

FIG. 9a shows the experimentally measured spectra for the DSRR structure array for tensile strains of up to 50%. ESEM images of structures initially, under various amounts of strain, and relaxed are also shown.

Figure 9B:
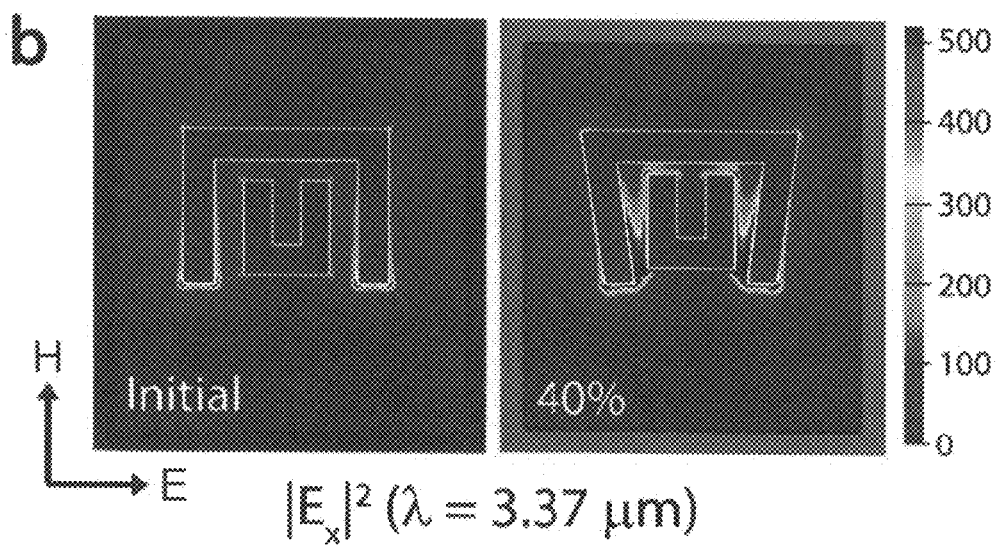

FIG. 9b shows electric field intensity plots at the vibrational mode resonant wavelength (3.37 μm) for the initial structure and at 40% strain.

Figure 9C:
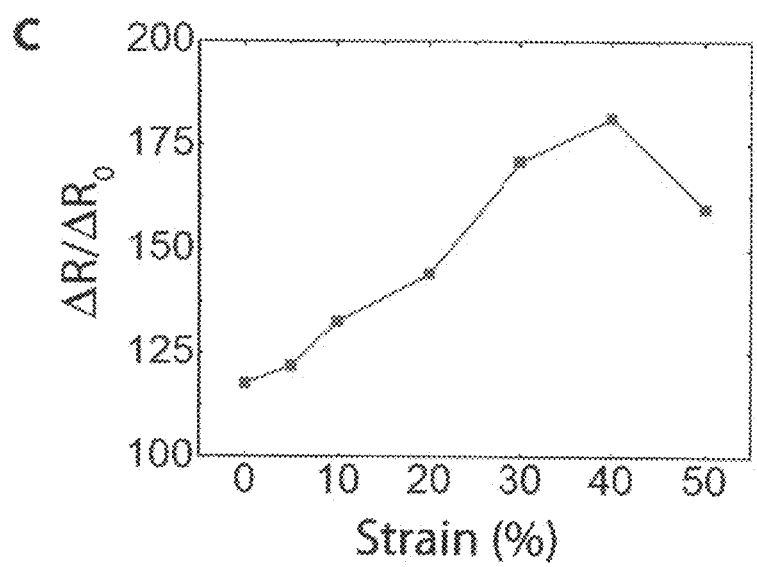

FIG. 9c shows the signal enhancement for the C—H stretch vibrational mode as a function of observed tensile strain.

FIG. 10a shows the experimentally measured spectra of the Dolmen-resonator structure for observed strains of up to 50%. The schematic of the dolmen-resonator structure with dimensions is shown as an inset to the graph.

FIG. 10b is an ESEM image showing the unit cell of FIG. 10a initially and the electric field density at $\lambda_1$ and $\lambda_2$, the two reflection peak positions.

FIG. 10c is an ESEM image for the unit cell of FIG. 10a under 50% tensile strain and the corresponding electric field intensity plots at $\lambda_1$ and $\lambda_2$.

FIG. 10d is an ESEM image for the unit cell of FIG. 10a after relaxation and the corresponding electric field intensity plots at $\lambda_1$ and $\lambda_2$.

Figure 11A:
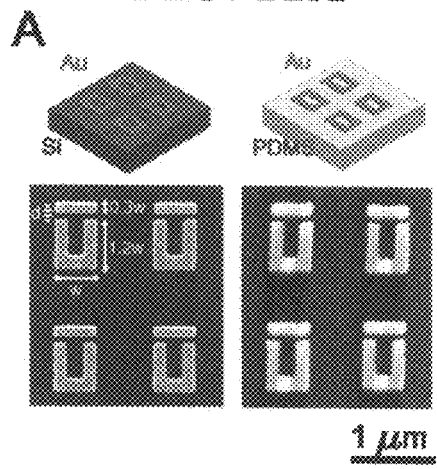

FIG. 11A depicts SEM micrographs of a representative array of split ring resonators (SRRs) both before and after transfer to the PDMS substrate. The schematics serve as labels to the micrographs. For the structures shown here, w=500 nm, d=40 nm, and the other dimensions scale as indicated with w.

Figure 11B:
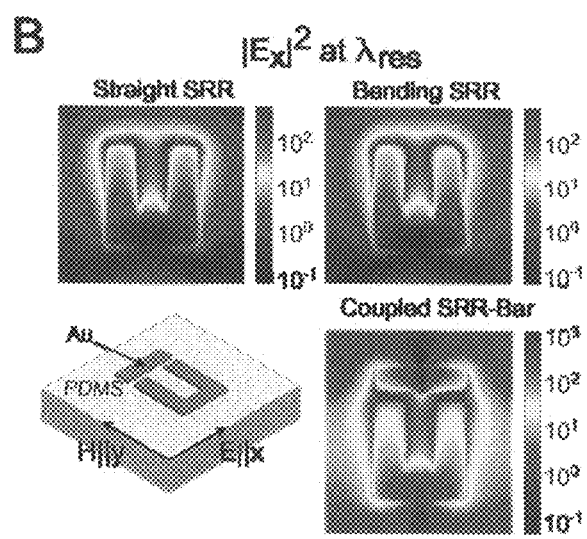

FIG. 11B shows the electric field intensity plots for three different resonator cases, each at their respective resonant frequency. The straight SRR case shows the simulated field for a basic uncoupled SRR. The bending SRR case includes the deformation of the SRR arms when the resonators are attached to a compliant substrate. The bottom right panel shows the coupled SRR-bar system and the schematic in the bottom left shows the electric field polarization relative to an individual resonator.

Figure 12A:
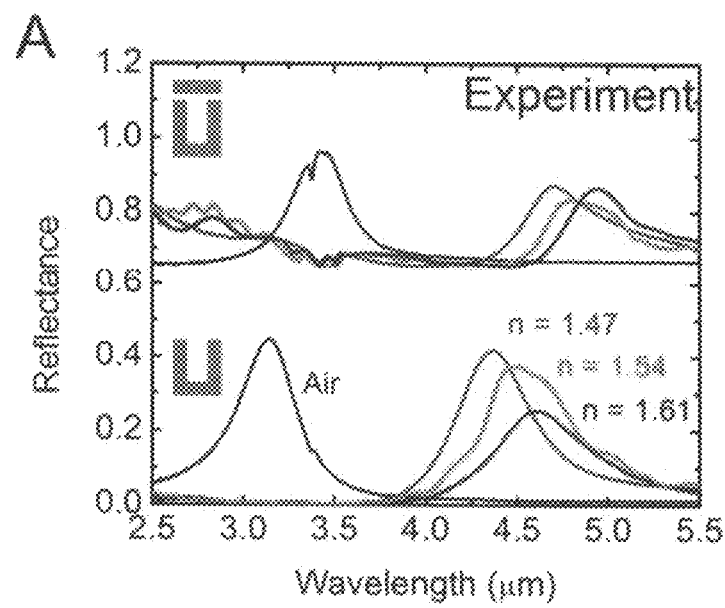

FIG. 12A depicts the experimentally measured FTIR reflection spectra for representative arrays. The bottom set of data is for an array of uncoupled resonators in air and three different optical matching fluids. The index of the fluids used is indicated in the plot. The coupled data are for an array of SRR-bar resonators with a coupling distance of 40 nm.

Figure 12B:
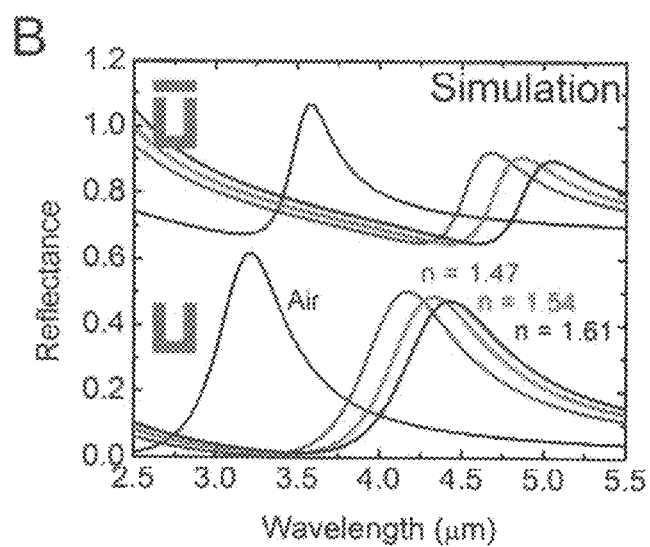

FIG. 12B depicts the simulated response for uncoupled and coupled arrays.

FIG. 13A depicts environmental SEM (ESEM) images of representative structures on PDMS.

FIG. 13B depicts plots of the experimentally determined figure of merit (FOM) values of resonators with w=500 nm. The FOM is the sensitivity in terms of nm/RIU divided by the full-width at half maximum (FWHM) of the resonant peak in air. The unfilled data point at a coupling distance of 500 nm refers to the uncoupled SRR, i.e. without a bar.

FIG. 13C depicts a plot of the simulated data for the same resonators as FIG. 13B. Two different uncoupled resonator cases are simulated—the "straight SRR" and "bending SRR".

FIG. 13D depicts environmental SEM (ESEM) images of smaller resonator structures on PDMS.

FIG. 13E depicts plots of the experimentally determined figure of merit (FOM) values of the smaller resonator structures of FIG. 13D. Here, the uncoupled distance is equal to the width of the resonator, 220 nm.

FIG. 13F depicts a plot of the simulated data for the same resonators as FIG. 13D.

FIG. 14A depict the FTIR reflection spectra data for arrays of resonators on Si functionalized with pMA. The coupling distance is indicated in the labels. The dotted line shows cross-polarized data for the array at a 40 nm coupling distance. The black line is the spectrum for an 800 nm thick film of pMA on glass. The structure of the pMA molecule is inset in the figure. The data are offset for clarity.

FIG. 14B depicts plots of electric field intensity at the resonant wavelength ($\lambda$=6.25 μm) for the 40 nm coupled resonator system. The simulated data for both the x-y plane (left) and the x-z plane (right) are shown. The x-z plane is taken at the point indicated by the dotted line on the x-y plane panel.

FIG. 14C shows the enhancement factor values for each vibrational mode signal as a function of coupling distance.

Figure 15:
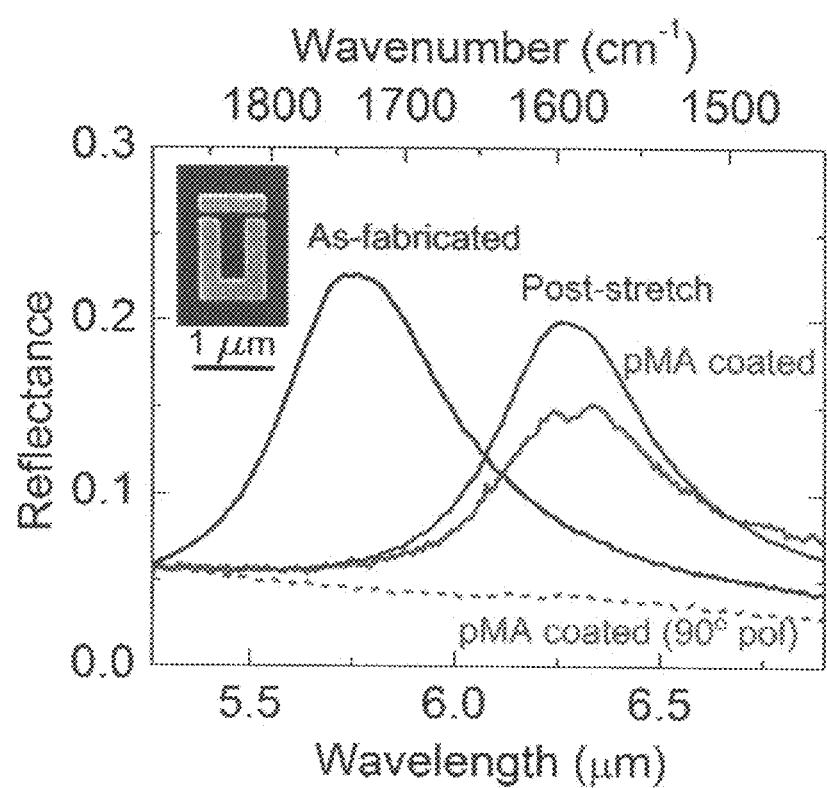

FIG. 15 depicts the FTIR reflection spectra for an array of resonators on PDMS with a coupling distance of 60 nm. The "As-fabricated" response for the resonator array is shown in blue, the dark red line shows the spectrum for the array of resonators after stretching to the appropriate resonance, and the red line indicates the response for the array after functionalizing with pMA. The dotted line shows the cross-polarized measurement for the functionalized array.

DETAILED DESCRIPTION

According to embodiments of the present invention, a stretchable compliant substrate is used to tune the resonant frequency of a metamaterial in the near-infrared by changing the distances and thus the coupling strength between pairs of resonator elements. In particular, the deformation of the compliant substrate is used to effect the tuning. According to embodiments of the present invention, a polymer substrate can be used as the dynamic component of an active metamaterial, enabling mechanical deformation of the composite unit cells.

In embodiments of the present invention, a metamaterial structure comprises a flexible substrate, a metamaterial pattern on a surface the substrate, and a metal in the metamaterial pattern. The metamaterial structure is tunable by straining and relaxing the structure. The flexibility of the substrate enables the application of strain by mechanically stretching the substrate. The application of sufficient strain, and the subsequent relaxation of the substrate results in a shift in the resonant response of the metamaterial on the surface of the substrate. Accordingly, in some embodiments, the metamaterial structure includes a strained and relaxed substrate which has been strained to a degree sufficient to register a resonant response upon relaxation that is shifted relative to the resonant response of the initial (unstrained) substrate. The amount of strain required to register the shift in resonant response may vary depending on certain factors, including but not limited to the metamaterial pattern and/or the materials of the substrate and/or metals. In particular, in some embodiments, when the flexible substrate is subjected to about 5% or greater strain, and then subsequently relaxed, the resonant response of the relaxed substrate is shifted with respect to the response of the initial (unstrained) substrate. In these embodiments, when the substrate is subjected to less than about 5% strain, the resonant response of the relaxed substrate substantially matches the resonant response of the initial (unstrained) substrate. In some embodiments, however, the substrate must be subjected to about 10% or greater strain before the relaxed substrate will register a shift in the resonant response with respect to the initial (unstrained substrate). Specifically, in these embodiments, when the substrate is subjected to less than 10% strain, the resonant response of the relaxed substrate substantially matches the resonant response of the initial (unstrained) substrate. In still other embodiments, the substrate must be subjected to about 20% or greater strain before the relaxed substrate will register a shift in the resonant response with respect to the initial (unstrained substrate). In these embodiments, when the substrate is subjected to less than about 20% strain, the resonant response of the relaxed substrate substantially matches the resonant response of the initial (unstrained) substrate.

Additionally, while there is no upper limit on the amount of strain that the flexible substrate may be subjected to, too much strain may cause significant distortion, or damage, of the substrate (e.g., cracking or tearing), which is undesirable. As such, the amount of strain that the flexible substrate may be subjected to will be dependent on the material of the substrate. In keeping with this, the flexible substrate may be subjected to any amount of strain that it is capable of withstanding without significant distortion. In some embodiments, for example, depending on the material of the compliant substrate, the substrate can be subjected to up to 100% strain. In general, however, most compliant substrates can be subjected to up to about 50% strain without registering significant damage. Accordingly, in some embodiments, the substrate may be subjected to about 5% to about 50% strain, in other embodiments may be subjected to about 10% to about 50% strain, and in still other embodiments may be subjected to about 20% to about 50% strain.

To pattern the metamaterials on the surface of the flexible substrate, the metamaterial designs are first patterned in lithographic resist on a handling substrate, a metal layer is applied to the pattern, and the flexible material of the flexible substrate is applied to the surface of the metal and the handling substrate. The handling substrate is then removed by peeling or etching, leaving a flexible substrate having a surface patterned with the metamaterial structures.

The handling substrate is not particularly limited, and selection of a suitable handling substrate is within the skill of those of ordinary skill in the relevant art. However, Si wafers are a nonlimiting example of a suitable handling substrate.

The flexible material of the flexible substrate is also not particularly limited. However, the material should be capable of mounting the metamaterials on its surface, and capable of stretching to a strain rate of at least about 50% without registering significant distortion. In addition, the flexible material should be capable of surviving the handling substrate removal process (e.g., the etching or peeling off of the Si handling substrate). Nonlimiting examples of suitable flexible materials for the flexible substrate include flexible polymers (such as, e.g., polydimethylsiloxane (PDMS) and polyimide), rubbers (such as, e.g., polybutadiene rubbers), and vinyl acetates.

In addition, the metamaterial patterns are also not limited. The stretchable substrates of embodiments of the present invention are applicable to all types of metamaterial patterns. The selection of a particular metamaterial pattern for a given application, when not in stretchable form as described in the present application, is within the skill of those of ordinary skill in the art. Similarly, the metal of the metamaterial patterns are not limited, and can be any suitable metal. Nonlimiting examples of suitable metals include Au, Ag, Cu and Pt. In some embodiments, the metal layer may be functionalized, for example, with mercaptopropyl trimethoxysilane (MPT), or the like.

The tunable metamaterial structures according to embodiments of the present invention have numerous applications, as would be appreciated by those of ordinary skill in the art. Among these applications is the use of the structures in resonantly enhanced infrared absorption spectroscopy and refractive index sensing. These applications are discussed in more detail below. In some embodiments, for example, the metamaterial structures may enhance the IR absorption signal (or vibrational mode signal) of an analyte, e.g., p-mercaptoaniline. In these embodiments, the analyte (e.g., p-mercaptoaniline) is adsorbed to a surface of the flexible substrate containing the metamaterial patterns and the metal. The metamaterial structures according to embodiments of the present invention may be used to sense any of various analytes, and the identification of such analytes would be within the skill of those of ordinary skill in the art. p-mercaptoaniline is but one nonlimiting example of an analyte that the metamaterial structures according to embodiments of the present invention can sense. The enhancement of the analyte signal by the metamaterial structures is described in further detail below in connection with the resonantly enhanced infrared absorption spectroscopy and refractive index sensing applications.

Metamaterial designs are typically limited to a narrow operating bandwidth that is predetermined by the fabricated dimensions. Various approaches have previously been used to introduce post-fabrication tunability and thus enable active metamaterials. Here, the mechanical deformability of a highly compliant polymeric substrate is used to achieve dynamic, tunable resonant frequency shifts greater than a resonant linewidth. The effect of metamaterial shape on the plastic deformation limit of resonators is also investigated, and it is found that, for designs in which the local strain is evenly distributed, the response is elastic under larger global tensile strains. The plastic and elastic limits of resonator, deformation are explored and the results indicate that, once deformed, the resonators operate within a new envelope of elastic response. It is also demonstrated that the use of coupled resonator systems adds an additional degree of freedom to the frequency tunability, and it is shown that compliant substrates can be used as a tool to test coupling strength. Finally, this disclosure illustrates how compliant metamaterials could be used as infrared sensors, and show enhancement of an infrared vibration absorption feature by a factor of 225.

Stretchable electronics have recently garnered increasing interest. Indeed, flexible, stretchable platforms for electronics are an increasingly popular concept because of the ease with which they could be integrated with other devices. In the realm of plasmonic structure design, elastomeric substrates have been used to alter the resonant response of nanoparticle dimers and gratings. However, though mechanical deformation of elastomeric substrates has been used to induce spectral shifts in the resonance of nanophotonic structures such as nanoparticle dimer extinction and gratings, the reported tunability range was limited. Here, it is shown that mechanical actuation of a surface can be used to achieve a linewidth shift in the resonant response of a metamaterial surface.

Figures 1A, 1B:
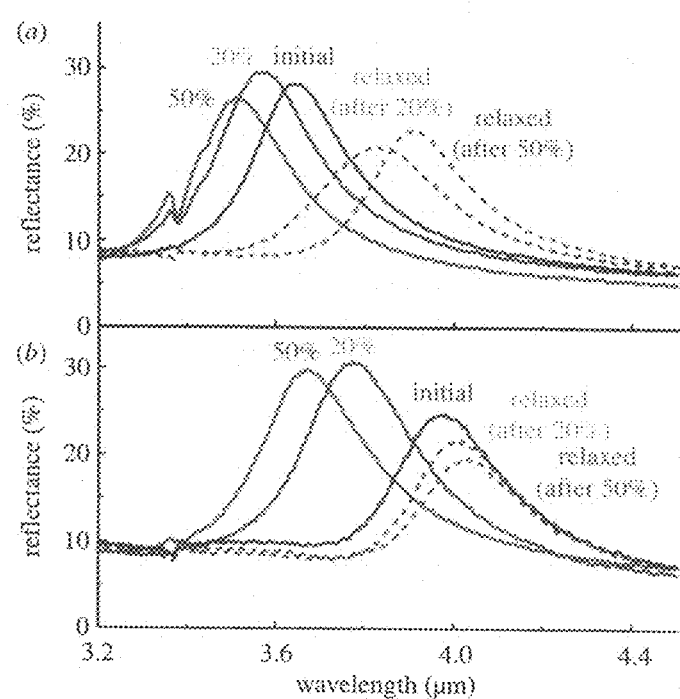
FIG. 1a is a graph comparing the FTIR spectra for the initial plastic deformation of the d=50 nm SRR-nanowire-coupled resonator pair under varying tensile strains up to 50%.
FIG. 1b is a graph comparing the FTIR spectra after subsequent deformation of the resonator pair of FIG. 1a for tensile strains of up to 50%. The initial position is the same as the "relaxed (after 50%)" position in FIG. 4a, and the 0% strain position ("relaxed (after 20%)" and relaxed (after 50%)") data are shown to demonstrate the elastic nature of the resonator after deformation.

Full linewidth tunability is an important goal for any active metamaterial as it is critical for a number of applications, including optical filters and modulators. In FIG. 1$a$, the effects of larger strain on the d=50 nm SRR-bar coupled resonator system is demonstrated. For a strain of 20%, the resonant peak blue-shifts to 3.56 µm from the initial resonance position of 3.64 µm. Instead of relaxing back to the initial resonance, the peak relaxes to a frequency that is further red-shifted owing to permanent deformation of the PDMS in the gap. Similar behavior occurs for a strain of 50% where the resonant peak shifts to a wavelength of 3.51 µm and then relaxes back to a resonant frequency that is even further red-shifted at 3.91 µm. Though the 50% strain resonant peak position is not a full linewidth shift from the initial position, it is a linewidth shift from its relaxed position.

Elasticity of the response is an important criterion for active metamaterials, and it is shown here, as in previous work, that for strains of more than 10%, the samples have an inelastic response. In FIG. 1$b$, however, the sample response after deformation to a tensile strain of 50% is examined. In this case, the initial position is the same as the 'relaxed (after 50%)' position in FIG. 1$a$. The resonant peak position shifts to 3.77 µm for a strain of 20%. Of particular interest here is that the sample relaxes back to the initial resonance. Similar behavior is observed when the sample is stretched to 50% strain and the peak blue-shifts by 330 nm to 3.67 µm, a full linewidth from the initial resonance. These data show that, once deformation has been introduced to a sample, there is a new elastic deformation limit. This means that subsequent loading cycles, like that shown in FIG. 1$b$, give information about sample strain history. In addition, it shows that deformation can be initially introduced to achieve an elastically tunable response.

According to embodiments of the present invention, the compliant metamaterials can be used for any suitable application, including, but not limited to tunable resonator structures, which can, in turn, be used for resonantly enhanced infrared absorption spectroscopy and refractive index sensing. These applications are described in detail in below.

Tunable Resonator Structures

The results presented here represent the first demonstration of broad tunability of metamaterials via the elastic and plastic deformation of compliant substrates and, surprisingly, the results show that the nanoscale resonator arrays can be subjected to tensile strains as high as 50±1% without delamination or distortion of the metallic elements. Although flexible metamaterials have been fabricated to operate at microwave and terahertz frequencies, compliant tuning of metamaterials has not previously been shown. Specifically, although the utility of flexible metamaterials operating at microwave and terahertz frequencies has been demonstrated, the present invention is the first greater-than-linewidth tuning in the near infrared. Indeed, as discussed above, embodiments of the present invention are directed to compliant substrates that can be used to tune the resonant frequencies of various split ring resonator (SRR) designs, and additional embodiments are directed to coupling two resonators, which enables broader tunability. Also, the experimental results discussed heft investigate the dependence of the mechanical deformation on resonator shape and the limits of plastic and elastic tunability of polymer-embedded resonator systems. Indeed, the results demonstrate tunable Fano resonances utilizing the mechanical deformation of compliant dolmen-type resonator arrays.

The metamaterial structures investigated were planar, coupled split-ring resonator (SRR) arrays in which the resonant frequency depends on the geometry of the SRR and the complex refractive index of the metamaterial substrate. At optical frequencies, U-shaped SRRs have been extensively studied and can be modeled as electrical LC resonators with a resonant frequency of $\omega_0 \sim (LC)^{-1/2}$, where the effective capacitance (or distributed capacitance) C depends on the gap size (i.e., it is inversely proportional to the distance between the SRR arms), and the inductance (or distributed inductance) L is proportional to the total effective length of each SRR (i.e., it is dependent on the total path length of the resonator). This resonant frequency can be altered by changing the geometry of the SRR or by introducing a coupling element, such as a nanowire. This introduces an additional parameter, the coupling constant, that provides further control over the resonant wavelength of metamaterial structures. The coupling constant depends on the distance between the resonator pairs, and it has been previously reported that for passive structures, changing the coupling distance results in a significant shift in the resonant frequency response. See Aydin, K.; Pryce, I. M.; Atwater, H. A. Opt. Express 2010, 18, 13407-13417, the entire content of which is incorporated herein by reference.

The approach presented here is to adhere 100 nm thick Au SRRs to a 1 mm thick PDMS substrate. The metamaterial arrays are patterned on Si wafers using electron beam lithography. Electron beam evaporation is used to deposit 100 nm of Au, which is coated with a monolayer of 3-mercaptopropyl trimethoxysilane (MPT) under 50 mTorr vacuum. The MPT creates an Au—S bond at the surface that preferentially binds with the PDMS. Low-bias inductively coupled plasma reactive ion etching (ICP-RIE) with $SF_6$ is used to selectively remove the Si wafer leaving a freestanding 1 mm thick PDMS substrate with 100 nm thick metallic patterns on top.

In more detail, a hard/soft nanolithographic pattern transfer technique was used to investigate a number of different SRR designs. SRR arrays were patterned in polymer resist over 100×100 μm squares by electron beam lithography on a sacrificial Si substrate. Au was evaporated using electron beam evaporation to create 100 nm thick patterns, as shown in FIG. 2a (step 1). Specifically, FIG. 2a (step 1) shows how the SRRs are lithographically patterned on a Si handle wafer. The SRR-nanowire-coupled resonator pair is used as an example, but the same approach is followed for all resonator types. The scanning electron micrograph shows the resonators as patterned on Si.

The Au was functionalized with a monolayer of 3-mercaptopropyl trimethoxysilane (MPT) under a 50 mTorr vacuum. This served to improve adhesion between the Au resonators and a polydimethylsiloxane (PDMS) layer that was cured on top of the patterns, as shown in FIG. 2b (step 2). Specifically, FIG. 2b (step 2) shows how the Au is functionalized with MPT and embedded in PDMS.

The Si handle substrate was selectively removed via low-bias inductively coupled plasma-reactive ion etching (ICP-RIE) with $SF_6$, leaving free-standing PDMS substrates patterned with multiple arrays of Au SRRs, as shown in FIG. 2c (step 3). Specifically, FIG. 2c (step 3) shows that the Si wafer is back-etched via RIE to leave a free-standing PDMS substrate. The SEM in this panel shows the fidelity of the pattern transfer.

The schematics in FIGS. 2a, 2b and 2c outline the process and show how a typical pattern, an SRR with a bar resonator, is transferred to the PDMS. FIG. 2a shows an electron micrograph of the pattern on the Si wafer after electron beam patterning. The micrograph in FIG. 2c shows the pattern on the PDMS after transfer, demonstrating that the nanostructures did not undergo deterioration in the transfer process. The transfer process is reproducible for a number of designs with nanometer feature sizes and has been replicated for many different samples.

Mechanical deformation of the substrate is used to stretch the resonators apart, changing both the capacitance of the SRR gap and the coupling strength between resonator pairs. A custom-built stage was used to mechanically deform the samples, change the resonator shape and shift the resonant frequency. The strain is defined as $(1-l_0)/l_0 \times 100\%$, where $l_0$ is the initial length of the sample and 1 is the stretched length. The samples were characterized via environmental scanning electron microscopy (SEM) to determine the mechanical deformation to the individual resonators. A Fourier transform infrared (FTIR) spectrometer in reflection mode was used to characterize the effect of strain on the resonance of the SRRs. The reflectance was normalized to an Au reflection standard.

FIGS. 3a and 3b show metamaterial arrays on PDMS before and after stretching, respectively. The environmental scanning electron microscope (ESEM) image in FIG. 3b shows the extent of deformation observed for a strain of 50±1% in the y-direction. As noted above, the strain is defined as $(1-_0)/l_0 \times 100\%$, where $l_0$ is the initial length of the sample and the error is 1%. Different elements can be coupled to the SRR structure to change the operating frequency. Several different samples were examined, some of which are shown in FIG. 3c with dimensions, including: SRR-bar, asymmetric coupled SRR (ACSRR), square SRR (sqSRR), and double SRR (DSRR) arrays.

FIG. 4 shows the response of arrays of SRR-bar and ACSRR structures for strains of up to 50%. ESEM images of 4×4 arrays of unit cells are shown for the initial structures, the samples under 50% strain, and the samples after relaxation (FIGS. 4a and 4c). The custom-built stage was used to uniaxially stretch the compliant substrate. The coupling distance changes, as does the array period both parallel and perpendicular to the strain axis. The optical response of each sample was measured using Fourier Transform Infrared (FTIR) spectroscopy in reflection mode, and the spectra for the SRR-bar structures are shown in FIG. 4b. The observed resonance shifts are due to changes in coupling between the resonators and that the changing array period has a negligible effect. The spectrum has a reflection peak at 3.65 µm corresponding to the hybridized antisymmetric electromagnetic resonance of the unit cell. See Aydin, K.; Pryce, I. M.; Atwater, H. A. *Opt. Express* 2010, 18, 13407-13417, the entire content of which is incorporated herein by reference. Here, the antisymmetric resonant mode of the array is shown, although there is also a symmetric resonance, which is discussed below. The sample was first strained 10% in the y-direction resulting in a blue shift of the resonant wavelength by 30 nm. The blue shift of the resonance frequency is due to the reduction in coupling strength when the coupled resonator elements are separated. The sample was then relaxed and the resulting data are coincident with the initial spectral position showing that for up to at least 10% strain the tuning is elastic in nature.

While elastic tunability of a metamaterial may be desirable, inelastic deformation could prove to be of particular importance for post-fabrication tuning. For tensile strains of 20 and 50%, the reflection peak shift by 80 and 140 nm, respectively, is observed. This corresponds to an initial SRR-bar distance of 50 nm and a stretched distance of 56 and 71 nm, as obtained from statistical analysis of ESEM images of arrays. After inducing a tensile strain of 50%, the elastomeric substrate was relaxed. The reflection peak position after relaxation is red shifted by 260 nm from the initial resonant peak, suggesting that the nanowire is closer to the resonator than in the original position. This is corroborated by the ESEM image (FIG. 4a), which shows that the SRR-bar coupling distance is now 35 nm due to the permanent plastic deformation of the PDMS. Full-field electromagnetic simulations of the reflectance of the metamaterial arrays, calculated as described in Aydin, K.; Pryce, I. M.; Atwater, H. A. *Opt. Express* 2010, 18, 13407-13417, the entire content of which is incorporated herein by reference, are shown in FIG. 4b and these data agree well with the experimental results.

Changing the geometry of the resonant element from a nanowire to an asymmetric SRR reduces the resonant line width, improving tunability. FIG. 4d shows the reflectance data for the array of ACSRRs. The initial reflection peak position is observed at 3.90 µm for a coupling distance of 60 nm. Elastic tuning was achievable up to 10% and, in this case, the peak was blue shifted 70 nm, double the wavelength shift for the SRR-bar structure. For strains of 20 and 50%, the coupling distance is increased to 72 and 85 nm and the resonance is observed at 3.78 and 3.74 µm, respectively. After relaxing the sample, the SRRs are closer than in the original sample and the coupling distance was reduced to 45 nm, corresponding to a final resonance position of 4.07 µm. The simulation data for the ACSRR array are shown in the bottom panel of FIG. 4d and agree well with the experiment.

Tunability ranges vary for the different arrays due to the sensitivity of the resonant wavelength shift on the coupling mechanism of the SRR designs. To compare the effect of strain on the tunability range for various resonator designs, a figure of merit (FOM) is defined as the resonant wavelength shift, $\Delta\lambda$, divided by the full width at half-maximum (FWHM) of the initial reflection peak. The top panels of FIGS. 5a, 5b, 5c and 5d compare FOM as a function of mechanical strain. Tensile strains of up to 50% were induced in the y-direction and 25% in the x-direction. Finite element modeling (FEM) results showing maps of normalized strain in the top layer of PDMS for each of the four SRR unit cells are displayed in the bottom panels with arrows indicating displacement vectors. For the sqSRR structure (FIG. 5a), a maximum FOM of 0.4 for 50% strain is measured. From the FEM simulations of strain, it can be seen that stretching along the y-direction brings the arms closer, resulting in a decrease of the sqSRR gap. As a result, the effective capacitance increases, red shifting the resonant wavelength. The converse is true for stretching in the x-direction. With this simple sqSRR design, mechanical tuning can only affect the gap capacitance.

To increase the tunability range, more complex designs are necessary. Coupled resonators, such as the DSRR (described in Liu, N.; Guo, H. C.; Fu, L. W.; Schweizer, H.; Kaiser, S.; Giessen, H. *Phys. Status Solidi B* 2007, 244, 1251-1255, the entire content of which is incorporated herein by reference) (FIG. 5b) are explored, for which the FOM can be increased to almost 0.6. Plotting the FOM data shown in FIGS. 4a, 4b, 4c and 4d for the SRR-bar and the ACSRR structures, it is noted that increased coupling can indeed yield higher tunability. For the SRR-bar structure, a maximum FOM of 0.6 is achieved for strain applied along the y-direction and 0.4 for strain applied along the x-direction (FIG. 5c). For the ACSRRs, line width tunability is achieved by stretching the array in either direction (FIG. 5d). Coupled SRRs of differing size yield narrow electromagnetic resonances, and thus the FOM is highest for the ACSRR configuration.

Mechanical modeling for the DSRR shows that as the structure is strained, the arms of the outer SRR bend inward, increasing the coupling with the inner SRR and, in turn, the FOM. In the case of the SRR-bar and the ACSRR, however, the modeling shows that as the coupling element stretches away from the SRR, the highest region of strain is located in the gap and the displacement vectors show that these structures stretch uniaxially and do not experience bending as in the DSRR or sqSRR structures. This understanding of the nanomechanics provides useful insight for designing coupled resonators at the nanoscale for certain types of deformation and predicting the consequent mechanical and optical behavior.

Coupled systems composed of asymmetric resonator elements have symmetric and antisymmetric resonances. Above, only the antisymmetric resonances are reported for the SRR-bar and ACSRR cases, as the amount of tuning is larger and more strongly dependent on the coupling distance than for the symmetric resonance. In FIG. 6, the wavelength range is extended in order to show how both the symmetric and the antisymmetric mode are affected by the sample strain. In the case of the SRR-bar, the symmetric mode, which is largely due to the nanowire resonance, is almost completely unaffected by changing the coupling distance with the other resonator. This was discussed in greater detail in previous work. See Aydin, K.; Pryce, I. M.; Atwater, H. A. *Opt Express* 2010, 18, 13407-13417, the entire content of which is incorporated herein by reference.

Basic Split Ring Resonator Designs

In this study, a circular SRR (CSRR) design (FIG. 7a) was compared with a square SRR (sqSRR) design (FIG. 7b). The initial resonance at 5.04 µm (dashed line) is for the pattern after transfer from the Si to the PDMS and prior to stretching. Straining the resonators in the direction parallel to the gap caused the gap to decrease and the capacitance to increase. As is evident from the expression for $\omega_0$, increasing the capacitance will decrease the resonant frequency and red-shift the resonant wavelength. For a strain of 10%, the resonance shifts by 60 nm to 5.10 µm. The resonators were strained up to 50%, which red-shifts the resonance by 140 nm to 5.18 µm. The total path length of the sqSRR is shorter than that of the CSRR and, consequently, the initial resonance is at a shorter wavelength. This is indicated by the leftmost dashed line and occurs at 4.56 µm (FIG. 7b). For the sqSRR, it is found that stretching the structure to a global strain of 10% induces a shift of 60 nm to 4.62 µm, while a strain of 50% shifts the resonance by 140 nm to 4.70 µm.

Although the induced shifts in resonance are the same for both of these structures, there is a noticeable difference between the CSRR and the sqSRR structures. When the samples are allowed to relax after stretching to 50% strain, the resonance of the CSRR (FIG. 7a) moves to a value between the initial resonance and the fully strained resonance, whereas the sqSRR resonance remains at the fully strained resonance. In order to better understand the mechanical deformation, the structures were modeled using finite-element method (FEM) continuum mechanics calculations. The results of these calculations are shown in the strain maps in FIGS. 7a and 7b. The color intensity of the image indicates the local strain induced for 10% global strain, while the arrows show the displacement. It is evident that, for the CSRR, the strain is distributed around the outside of the Au, with small regions of high strain concentrated at the gap. The strain on the sqSRR, however, is highly localized at the corners of the resonator. This high strain density causes irreversible deformation of the Au-PDMS system upon stretching. These results are corroborated by the environmental SEM images shown in FIGS. 7a and 7b.

In the case of the CSRR design, the SEM micrograph shows that the pattern changes much less dramatically upon transfer to the PDMS. When the sample is relaxed, the gap size decreases, but the shape of the ring is not distorted. For the square ring, the shape is already slightly distorted after transfer to the PDMS and, after relaxing, the arms are obviously bowed inwards. Both of these structures are useful for guiding future resonator designs. For designs where an elastic response is important, it would be desirable to ensure that there are no regions of high strain density upon stretching. For designing resonators where deformation is used to permanently tune the resonance to a specific value, high regions of local strain could be exploited to give predetermined resonator shapes.

Coupled Resonator Systems

The basic split ring designs allow control over the capacitance but lead to limited tuning of the resonance. In order to achieve linewidth-scale tunability of the resonant frequency, another resonator is introduced to the system in such a way that the resonators are coupled. By changing the distance between the coupled resonators, the coupling constant can be affected, changing the resonant frequency. Passive structures have been used to show that a change in the coupling constant shifts the resonant frequency. See Aydin, K., Pryce, I. M. & Atwater, H. A. 2010 "Symmetry breaking and strong coupling in planar optical metamaterials," *Opt. Express* 18, the entire content of which is incorporated herein by reference. According to embodiments of the present invention, asymmetric coupled SRRs were also used to show how the resonant hybridization effect of the two resonators can be exploited to demonstrate linewidth tunability on a compliant substrate.

In FIGS. 8a and 8b, a nanowire resonator coupled to a basic 'U'-shaped resonator is introduced. The top line shows the resonant frequency for a nanowire-SRR system where the distance between resonators, d, is 110 nm. Three other arrays of nanowire-SRRs were patterned with distances of 90 nm, 70 nm and 50 nm. The electron micrographs of each of these designs on Si prior to transfer are shown to the right of the FTIR spectra. The dashed lines indicate the shift of the resonant peak with 5% strain. In the case of the d=110 nm system, 5% strain causes no shift in the resonant peak position. As the initial coupling distance decreases, however, the introduction of 5% strain does cause a shift in resonance. For the d=90 nm case, the resonance shifts 10 nm, and, for the d=70 nm resonator pair, the peak shift is 50 nm. Finally, for the d=50 nm system, the peak shifts by 80 nm from 3.65 to 3.57 µm, a significant fraction of the linewidth. This illustrates that, for systems where the resonators are closer together and thus more strongly coupled, small changes in the coupling distance will have a more pronounced effect on resonant peak position.

As noted above, compliant metamaterial surfaces could potentially be used as infrared sensors, or surface-enhanced infrared absorption substrates. In FIG. 8a, there is a noticeable reflection dip at 3.37 µm for the d=90 nm and d=100 nm cases. This absorption feature corresponds to the vibrational mode of a C—H stretch bond of PDMS. In FIG. 8b, the intensity of the reflection dip is plotted for each resonator divided by the reflection dip of the peak for bare PDMS. First, it can be seen that, as each resonator is strained and the enhancement moves from the solid to the dashed line, the enhancement of the absorption feature increases. This is a result of shifting the resonance of the SRR closer to the resonance of the vibrational mode. Additionally, the resonance of the d=110 nm SRR matches the vibrational mode most closely and hence results in over a 200-fold enhancement of the reflection dip before stretching. When this array of resonators is stretched, the enhancement of the absorption feature increases to 225. It is shown above that large strains could be applied to match the resonant frequency and increase the signal strength. Here, it is shown how a small amount of strain (5%) can be used to optimize the resonance of a resonator designed to operate at a particular frequency.

Nanophotonic metallic structures, such as plasmonic resonators and metamaterials that enhance the electric fields at the near-field, find applications in spectroscopic techniques such as surface-enhanced infrared absorption (SEIRA) and surface-enhanced Raman scattering (SERS) for biological and chemical sensing. Here, the mechanical tuning of the electromagnetic resonances of metasurfaces are exploited to amplify the signal of an infrared vibrational mode for surface enhanced reflection spectroscopy. In FIG. 9a, the measured reflectance spectra and representative ESEM images for various degrees of strain are shown for the DSRR array. In the reflection spectra of a PDMS substrate without metallic nanostructures, a weak absorption feature is observed at 3.37 µm which corresponds to the vibrational mode of the C—H stretch bond. Prior to stretching, the resonant wavelength of the metamaterial is 3.21 µm. A reflection dip associated with the coupling of the metamaterial resonance to the C—H stretch vibrational mode is observed.

By introducing mechanical strains up to 50%, it is possible to controllably tune the resonant wavelength of the metamaterial through the C—H vibrational absorption at 3.37 µm. For 40% strain, it is found that the peak of the metamaterial resonance is at 3.37 µm, coincident with the spectral position of the vibrational mode, resulting in increased absorption. Using full-field electromagnetic simulation, the total electric field intensities are calculated for the initial and 40% strained DSRR at 3.37 µm as shown in FIG. 9b. Given that the resonance of the initial DSRR is at a lower wavelength (3.22 µm), the electric field intensity at 3.37 µm is much lower than for the 40% strained DSRR. FIG. 9c reports the enhancement factor for the signal, $\Delta R/\Delta R_0$, which is the ratio of the resonator-enhanced absorption to the absorption from bare PDMS. For a resonator array in unstrained PDMS, the enhancement factor is 115, whereas at a strain of 40%, the absorption is enhanced by a factor of 180. A 1.6-fold increase is observed in the reflection signal upon optimizing the strain. The absorption enhancement is attributed to the electric field enhancement in "hot spot" regions between the two resonator legs and is maximized when the resonance of the metamaterial is matched to the C—H stretch vibrational mode as evident from the electric field intensity plots. The metallic nanostructures are on the surface of the substrate, thus it is only enhancing the reflection signal from the PDMS at the metal interfaces in the gap between resonator pairs. Given the in situ tuning capability of this type of structure, resonators could be designed to operate over a certain bandwidth and "focus" on peaks at particular frequencies. Mechanically deformable metamaterials could provide a more sensitive, broadband platform for both SEIRA and SERS measurements enabling sensing of low-concentration solutions of chemicals and biological agents.

The concept of mechanical tuning of electromagnetic resonances is also extended to plasmonic nanocavities. Recently, optical Fano resonances using coupled plasmonic nanostructures have received considerable interest. Here, a dolmen-type resonator is studied and it is demonstrated how mechanical tuning can be used to modulate the Fano response. The dolmen-resonator consists of two plasmonic components: (i) a pair of metal strips with a dark-mode (subradiant) resonance and (ii) a monopole antenna exhibiting a bright-mode (superradiant) resonance. Coupling these two resonant elements yields a Fano-type resonance. The experimental data for various strains are shown in FIG. 10a. The initial spectrum has distinct resonances at 2.72 and 3.18 µm with a reflection dip at 2.95 µm. When the dolmen-resonator array is strained along the y-direction, the coupling distance, $d_y$, increases causing a decrease in the coupling strength similar to that observed for the SRR-bar geometry. For 20% strain, it is observed that the $\lambda_1$ reflection peak blue shifts and the peak amplitude decreases with reduced coupling between the bright and dark modes. Then the sample is relaxed to its original position and the second reflection peak reappears. The same procedure is repeated for 50% strain, and it is noted that the second reflection peak becomes almost imperceptible (red line). The dashed red line in FIG. 10a shows the measured reflection spectra after relaxation, demonstrating the ability to recover the Fano resonance after inducing a tensile strain. It is observed that the reflection peak positions shift from the original positions due to plastic deformation upon stretching. This results in a decrease of $d_y$, leading to stronger coupling between resonators in a pair, and is evident in the ESEM image of the relaxed sample.

Digitized ESEM images of characteristic unit cells were used to calculate the total electric field intensities using full-field electromagnetic simulation. In FIG. 10b, the electric field intensities are plotted for the two reflection peaks, $\lambda_1$ and $\lambda_2$, prior to stretching. The electric field is strongly enhanced at the tips of the optical monopole antenna at $\lambda_1$ due to the dipole antenna resonance. At $\lambda_2$, the electric field is strongly localized between the optical antenna and the wire pair as a result of strong coupling between these two resonant elements. In FIG. 10c, the field intensities are plotted for 50% strain at $\lambda_1$=2.80 µm (left) and $\lambda_2$=3.22 µm (right). The coupling distance ($d_x$) increases, but the distance between the metal wire pair ($d_y$) decreases, resulting in an enhanced field between the metal wire pair for both resonances. At $\lambda_2$ however, the fields are not strongly localized between the wire pair and the optical antenna due to reduced coupling. The field intensity of the relaxed structure (FIG. 10d) is similar to the plot for the initial structure; however, the reflection peak positions are shifted to $\lambda_1$=2.82 µm and $\lambda_2$=3.35 µm. The $\lambda_2$ reflection peak is now aligned with the C—H vibrational mode and this signal is enhanced by a factor of almost 120.

Resonantly Enhanced Infrared Absorption Spectroscopy and Refractive Index Sensing Metamaterials can be designed to operate at frequencies from the visible to the mid IR, making these structures useful for both refractive index sensing and surface enhanced infrared absorption (SEIRA) spectroscopy. The mechanical deformation of compliant metamaterials (discussed above) can be used to create new types of tunable sensing surfaces. For split ring resonator (SRR) based metamaterials on polydimethylsiloxane (PDMS), refractive index sensing with figures of merit of up to 10.1 are demonstrated. Given the tunability of the resonance of these structures through the infrared, they are well suited for detection of the absorption signal of vibrational modes throughout the "molecular fingerprinting" regime. For split ring resonators on silicon, SEIRA enhancement factors on the order of $10^4$ are found. These results highlight the promise of post-fabrication tunable sensors and the potential for integration.

The design of nanophotonic sensors has garnered increasing interest as nanoscale fabrication becomes more sophisticated. New fabrication capabilities, advances in nanoscale analysis, and the improved computational power of full field electromagnetic simulations have led to a wealth of new designs based on the surface plasmon resonance of metallic structures. By tuning the geometrical properties of nanoscale features, shapes from crescents to bowtie antennas have achieved increasingly higher electric field enhancements which translate to improved sensitivity. In recent years, optical metamaterials, which are metallodielectric composites made up of subwavelength elements, have emerged as a new class of nanostructured architectures that enable the control and directed emission of light. While nanostructured plasmonic designs exhibit a characteristic dielectric permittivity resonance, metamaterial designs offer, in addition, tunable optical frequency magnetic resonance, which is more sensitive to the environment and exhibits a narrower linewidth. This resonance can be tuned from the visible through the infrared by changing the geometry of a characteristic resonator, and the linewidth can be narrowed via coupling of metamaterial unit cells.

A common approach to sensing is to detect small changes in the refractive index of the local environment by measuring the shift in frequency of the local surface plasmon resonance (LSPR). Plasmonic nanostructures have been used extensively as LSPR detectors since their resonant frequency is highly sensitive to changes in the dielectric constant of their environment. Typical wavelength and energy sensitivities are respectively in the hundreds to thousands of nm/RIU and tens to hundreds of meV/RIU. The highest reported values are for structures with sharp edges and coupled features with small inter-particle gaps. Functionalization of the metallic surfaces can be used to limit binding to specific analytes and this approach has been used to demonstrate a high degree of molecular sensitivity.

Refractive index sensors typically cannot rival surface enhanced spectroscopic techniques, such as surface enhanced Raman spectroscopy (SERS) and surface enhanced infrared absorption (SEIRA), which are widely used for sensing particular biological and chemical agents.

The sensitivity depends on the high electric field intensities of nanostructured surfaces leading to signal enhancement factors on the order of $10^8$ and $10^4$ for SERS and SEIRA, respectively. Similarly, the most sensitive SERS and SEIRA structures have sharp corners or edges which support significant enhancements to the local electric field intensity, resulting in detection limits on the order of zeptomoles for SEIRA and single-molecule spectroscopy using SERS substrates. SEIRA enhancements are weaker than those anticipated for SERS, as the SEIRA local field enhancement depends on $|E|^2$ versus $|E|^4$ for SERS. This combined with the difficulty of making a substrate that can operate over the entire infrared regime has led to far less research into SEIRA substrates. Metamaterial designs are well suited to this problem as they can be designed to operate throughout the infrared spectral range and have both sharp edges and strong inter-feature coupling required for high enhancement factors. There have been several previous demonstrations of both surface enhanced and refractive index metamaterial-based sensors in the literature. By building metamaterial-based sensors that operate in the near to mid-IR, the molecular fingerprinting regime, the narrow magnetic resonance could be exploited to both sense changes in refractive index and to enhance the signal of a particular vibrational mode.

Although metamaterials can be designed to work in any wavelength regime, their operating frequency is largely fixed by the constituent materials at the time of fabrication. Ideally the response would be tunable in situ to operate over a broader bandwidth and cover many different vibrational modes of the analyte. Here, a metamaterial system based on coupled split-ring resonators (SRR) adhered to a polymeric substrate, polydimethylsiloxane (PDMS), is used to demonstrate precise control over resonant frequency tunability and electric field enhancement. The resonant frequency of an SRR, $\omega_0$, is described by $\omega_0 \sim 1/(LC)^{1/2}$, where L is the inductance and depends on the resonator path length and C is the capacitance across the split in the resonator. By integrating the resonators with a compliant substrate, mechanical deformation can be used to change the capacitance of the gap and the coupling strength between resonators. This can be exploited to achieve up to linewidth tunability of the resonant response and to customize the response of the metamaterial post-fabrication. Here, a metamaterial-based sensor is presented that exploits the mechanical deformability of a highly compliant polymeric substrate to both detect small changes in refractive index and resonantly enhance the signal from several specific vibrational modes.

The sensitivity of both refractive index sensors and surface enhanced spectroscopic techniques depends critically on the intensity of the local electric field. Designing coupled resonator structures greatly enhances the local field at the resonant frequency, in a manner similar to the hybridization of plasmonic nanostructures. Thus, an analysis of the calculated field enhancements for coupled resonators is a good starting point. The resonator geometries utilized here are 100 nm thick Au SRRs coupled to Au bars (SRR-bar) on a PDMS substrate. As discussed above, the metamaterials are fabricated by patterning Au resonators on a Si handle wafer (FIG. 11A) and then transferring the patterns to a PDMS substrate using a hard/soft nanolithographic pattern transfer process. The SEM micrograph of the structures on PDMS (FIG. 11A—right panel) shows the fidelity of the pattern transfer process for a representative array of SRRs with a resonator width (w) of 500 nm and a coupling distance (d) of 40 nm. For the resonators utilized here, the SRR-bar aspect ratio remained constant as the dimension were varied, as indicated in FIG. 11A.

The samples were fabricated using the hard/soft nanolithographic pattern transfer technique described above. Specifically, arrays of 100 nm thick Au resonators are patterned via e-beam lithography on Si, with dimensions as shown in FIG. 11A. Each array is 100 µm long by 100 wide. The Au is functionalized using 3-mercaptopropyl trimethoxysilane (MPT) to improve adhesion to the polydimethylsiloxane (PDMS). PDMS with increased elasticity is made using a ratio of 1:12 curing agent to pre-polymer (Dow Corning Sylgard 184). The PDMS is cured for 1 hour at 70° C. on the patterns and a low-bias inductively coupled plasma reactive ion etch (ICP-RIE) with $SF_6$ is used to selectively remove the Si wafer leaving a free-standing 1 mm thick PDMS substrate with 100 nm thick metallic patterns (FIG. 11B).

The electric field intensity for three different resonators on PDMS is calculated via full field electromagnetic simulation at their respective resonant frequencies with the electric field polarized perpendicular to the resonator arms (FIG. 11B). In the top left panel, the electric field plot for an SRR with straight arms is shown. This simulation uses the measured geometry of a resonator on Si as determined from SEM micrographs of the patterned Au. When uncoupled resonators are transferred to the PDMS substrate, however, the stress in the PDMS causes the arms to bend inwards slightly. This bending causes an increase in the electric field intensity at the tips of the SRR, as made evident by the top right panel of FIG. 11B, which increases the sensitivity of these structures compared to straight SRRs. In the bottom right panel, the coupled SRR-bar case is plotted. The coupling in this unit cell increases the maximum field intensity by an order of magnitude relative to the uncoupled case. Coupling resonators in a metamaterial unit cell is thus important to the design of highly sensitive sensors or to any application that requires locally enhanced electromagnetic fields.

For the simulations, full-field electromagnetic wave calculations were performed using Lumerical, a commercially available finite-difference time-domain (FDTD) simulation software. A unit cell of the investigated structure is simulated using periodic boundary conditions along the x and y axes and perfectly matched layers along the propagation of electromagnetic waves (z axis). A broadband plane wave is incident on the unit cell along the +z direction, and reflection is monitored by a power monitor that is placed behind the radiation source. Electric fields are monitored by frequency profile monitors. The optical constants for Au were taken from Palik and a constant refractive index of 1.2 was used for the PDMS.

In order to further test the idea of using metamaterials as refractive index sensors, the SRR geometry shown in FIGS. 11A and 11B is considered. FTIR spectroscopy is used to measure the reflectance of the arrays across the IR spectrum. The samples are measured between λ=1.5 and 8 µm in a Fourier Transform Infrared (FTIR) microscope equipped with a liquid nitrogen cooled MCT detector. The measurements are taken in reflection mode at normal incidence and are the result of the coaddition of 64 scans with a 1.928 cm$^{-1}$ resolution. A $CaF_2$ polarizer is placed in the incident beam path and a KBr beamsplitter is used for all measurements. The reflectance data are normalized to a gold standard.

The experimentally measured spectra for both an uncoupled SRR and a coupled SRR-bar with d=40 nm are shown in FIG. 12A. For clarity, the width of the graph is limited to the region where the magnetic resonant peak is located. The electric resonance of the material is blue shifted from this peak. The resonance of the uncoupled SRR on PDMS in an ambient environment is 3.14 µm, and coupling of an SRR to a bar shifts the resonant frequency to 3.42 µm (FIG. 12A). In order to determine the sensitivity of the arrays as refractive index sensors, the reflection spectra were measured in three different index-matching fluids with refractive indices of 1.47, 1.54, and 1.61. The resonant frequency of the array is highly dependent on the dielectric constant of the surrounding environment, and increases cause the resonance to red-shift due to the increase in effective capacitance of the split gap. The resonance shifts from 4.37 µm in the n=1.47 index-matching fluid to 4.61 µm in the n=1.61 index-matching fluid. This represents a shift in the resonant wavelength, $\Delta\lambda_{res}$, from the initial measurement in air of 1.23 µm and 1.47 µm, respectively. The resonant peak shifts are more dramatic for the d=40 nm coupled resonator case, where the resonance is 4.71 µm in the n=1.47 index-matching fluid and 4.94 µm in the n=1.61 index-matching fluid, a red shift of 1.28 µm and 1.51 µm, respectively. The simulated data for these resonator arrays are shown in FIG. 12B. The uncoupled resonator data shown takes into account the resonator bending described previously and enables a much better fit to the experimentally obtained values than the straight SRR case, which is not shown here.

From the reflectance data, the sensitivities of the resonator arrays can be calculated, defined as the change in resonant frequency as a function of change in refractive index in units of nm/RIU. The sensitivity is then divided by the full width at half maximum (FWHM) of the resonant peak in an ambient environment to determine the figure of merit (FOM) of the resonator array. The FOM values for two different unit cell width geometries are reported, i.e., 500 nm and 220 nm. A representative SEM micrograph of a 4×4 array of resonators on PDMS is shown (FIGS. 13A and 13D). For the larger, w=500 nm, resonator array the calculated FOM values was up to 8.9 for a coupling distance of d=40 nm and a slightly lower value of 8.2 for a coupling distance of 55 nm. The unfilled data point in FIG. 13B where d=500 nm refers to the uncoupled resonator case. FIG. 13C shows corresponding simulation data for a number of different coupling distances and the calculated FOM values were 6.0 and 5.4 for coupling distances of 40 nm and 60 nm, respectively. The lower FOM values may be attributed to the broadening of the resonant peaks in simulation, as evident in FIG. 12B. The SRR is simulated with both straight arms and with bending arms as previously described, and it is found that the enhanced local field of the SRR while bending leads to an increase in the FOM from 3.3 to 3.7. The FOM values for the smaller resonator are higher than those reported for the larger unit cell, with values of 10.1 for a coupling distance of 30 nm and 9.3 for a coupling distance of 40 nm (FIG. 13B). As in FIG. 13A, the FOM value of 8.5 for the uncoupled resonator is plotted at a coupling distance equal to the resonator width of 220 nm and the line represents an exponential decay fit to the data. The simulated values are also reported for a number of points and the computed FOM was 8.9 for d=40 nm, 8.3 for d=60 nm, and 7.1 for the uncoupled, bent SRR case.

Reducing the coupling distance between resonators leads to higher FOM as a result of the higher local electric field for both resonator sizes. In addition, it is found that the FOM value will always be higher for a coupled resonator as the presence of the bar narrows the resonant peak. Part of the discrepancy between simulation and experiment may be attributed to inaccurate modeling of the SRRs on PDMS and it may be assumed that the average degree of bending of the SRR arms is actually higher for the ensemble than that predicted by the single SRR unit cell used in simulation. It is also possible that the SRR arms bend inwards when coupled to bar and this could also contribute differences for larger coupling distances where the stress is not offset by the bar. Nevertheless, these FOM data represent the highest values reported for nanostructures in the IR compared to previous reports of 3.9 for Au structures. This design is rivaled only by a three dimensional double nanopillar structure which has a FOM of 23 at a resonant wavelength of 1368 nm.

Table 1 summarizes the experimental results, and it is found that the highest FOM values can be engineered for the smallest coupling distances and the smallest resonator sizes. On the other hand, large SRRs are capable of achieving much higher sensitivity values (nm/RIU). One important feature of this approach is that resonators can be designed to span a broad spectrum. The resonant wavelength of the structures on PDMS in an ambient environment for a number of different sized resonators in addition to their sensitivities and FOM values are reported. The sensitivity in units of eV/RIU is also reported for comparison with other sensor geometries. The wide distribution of resonance values shows that resonators can be designed to work through most of the IR with limits being imposed, not by the fabrication technique or design stipulations, but rather by the characterization techniques available. For instance, the 800 nm SRR-bar geometry is not included in Table 1 because the resonance is red-shifted out of the range of the detector.

TABLE 1

Summary of the values obtained for different sizes of coupled and uncoupled resonators

| Structure | w (nm) | d (nm) | $\lambda_{res}$ (µm) | Sensitivity (nm/RIU) | Sensitivity (meV/RIU) | FWHM (nm) | FOM |
|---|---|---|---|---|---|---|---|
| SRR | 220 | — | 1.42 | 1192 | 497 | 141 | 8.5 |
| SRR-bar | 220 | 40 | 1.45 | 1225 | 488 | 121 | 10.1 |
| SRR | 500 | — | 3.14 | 2480 | 216 | 381 | 6.5 |
| SRR-bar | 500 | 40 | 3.33 | 2546 | 190 | 286 | 8.9 |
| SRR | 800 | — | 5.09 | 3366 | 116 | 521 | 6.5 |

In Table 1, resonator width, w, and coupling distance, d, are used to define the resonator geometry. $\lambda_{res}$ is the resonant wavelength in air, FWHM is the full width half maximum of the resonance peak in air, FOM is the figure of merit defined as sensitivity (nm/RIU)/FWHM (nm).

The ability to tune the response of these resonators either through fabrication or with in situ dynamic strain is also of interest for surface enhanced spectroscopic techniques, where alignment to particular vibrational modes is crucial for enhancement of the molecular signal. For example, the dips in the experimental data in FIG. 12A for the coupled resonator in air case (black line) near 3.3 µm are due to an overlap of the metamaterial resonance with the vibrational modes of the symmetric and antisymmetric C—H stretch bonds in the PDMS. The notch in the uncoupled resonator in air peak is also due to these modes. Here, the attention is focused on the IR absorption signals from the vibrational modes of p-mercaptoaniline (pMA) and how they can be enhanced using coupled SRR-bar nanostructures.

First, arrays of coupled Au SRR-bar resonators on Si with unit cell widths of 500 nm and coupling distances from 40 nm to 140 nm are used. This static structure emulates the behavior that can be induced mechanically by integrating the resonators with a compliant substrate as the resonant frequency shifts from 6.0 µm to 6.3 µm over this range of coupling distances. The surface of the coupled resonators is functionalized with a monolayer of pMA by leaving the sample in a 10 mM ethanolic solution overnight. The thiol group on the pMA binds preferentially to the Au and a monolayer is formed. The sample is then thoroughly rinsed with ethanol prior to measuring to ensure that only a monolayer remains bound to the surface of the Au. The pMA coverage was also confirmed using XPS measurements. The reflectance spectra after pMA functionalization are reported for each coupling distance (FIG. 14A). Three peaks were identified in the data corresponding to the δN—H mode at 6.20 μm (1614 cm$^{-1}$), the νC—C mode at 6.31 μm (1585 cm$^{-1}$), and the νC—C and δC—H vibrational modes at 6.73 μm (1485 cm$^{-1}$). As the coupling distance changes, the resonant peak shifts through these frequencies and the overlap of the metamaterial resonance with each vibrational mode results in pronounced dips in the reflection spectra.

The enhancement of the vibrational mode signals can be calculated relative to an 800 nm thick reference film of pMA (FIG. 14A—black line) and is dependent on the local field enhancement at the resonant peak. First, the dip in the reflection spectra is quantified as the difference, $\Delta R_{SRR}$, between the maximum and the minimum value of reflectance at each vibrational frequency. Maxima are found of 4.5% for the C—C stretch bond at 1585 cm$^{-1}$, 1.7% for the N—H delta mode, and 1% for the mode at 1485 cm$^{-1}$. In order to confirm that the observed signals are due to enhanced electromagnetic fields at the metamaterial resonance, the cross-polarized reflectance spectra for the d=40 nm SRR-bar is also reported (FIG. 14A—blue dotted line). This is corroborated by measurements (not shown here) of functionalized planar Au surfaces and arrays with resonant frequencies far from these vibrational modes where there is also no detectable pMA signal. The electric field intensity at 6.25 μm (1600 cm$^{-1}$) for both the x-y plane and the x-z plane of the d=40 nm SRR-bar is shown in FIG. 14B. The x-z plane cut is taken at a point just beyond the tips of the SRR arms, where the field intensity is highest (dotted white line). The near-field enhancement is strongest through the gap and along the sides of the SRR, and all regions with $|Ex|^2$ greater than $10^3$ are chosen to determine the electromagnetic hot spot region. The path length of the high intensity region is multiplied by the thickness of the Au, 100 nm, to give a surface area of 0.087 μm$^2$. Monolayer coverage of pMA to the resonators and a molecular cross-section on Au of 0.3 nm$^2$ are assumed, yielding approximately $4.4 \times 10^8$ active pMA molecules per SRR ($N_{SRR}$). The number of molecules contributing to the signal from the 800 nm thick pMA reference film is $1.2 \times 10^{13}$ molecules ($N_{ref}$). The signal enhancement factor (EF) for each vibrational mode is determined by comparing the ratios of the resonantly enhanced signals to the signals from the neat pMA according to EF=$(\Delta R_{SRR}/N_{SRR})/(\Delta R_{ref}/N_{ref})$, where $N_{SRR}$ is the number of molecules adsorbed in the high intensity region of the SRR, $N_{ref}$ is the number of molecules contributing to the signal from the pMA film, and $\Delta R_{ref}$ is the signal for each vibrational mode. The EF values for the vibrational modes at each coupling distance are reported in FIG. 14C. For the d=40 nm SRR-bar array, SEIRA enhancement factors for all modes on the order of $10^4$ were found, which is the same as other optimized nanostructured geometries. The high enhancement factors and the wide tunability of the approach enable access to any particular set of vibrational modes indicating that metamaterial designs may be of particular interest to the development of new SEIRA, as well as SERS, substrates.

Although the enhancement factors for resonators on Si are high, this approach lacks the in-situ tunability that may be possible with active metamaterial components. The coupled resonator metamaterials on PDMS were also evaluated as a potential SEIRA substrate. A major concern for this system, however, is the relatively low electric field intensity that is attainable. The electric field intensity observed for the SRRs on Si (FIG. 14B) is an order of magnitude higher than that observed for the resonators on PDMS (FIG. 11C) due to the much higher refractive index contrast of the Si with respect to the environment. The attractiveness of the PDMS system is the tunability of the resonant response post-fabrication, and it is shown above that the metamaterial resonance can be tuned by a full linewidth via mechanical distortion of the substrate.

Here, plastic deformation of the PDMS is used at the nanoscale to tune a resonator to the correct resonant frequency. A custom-built stage is used to induce tensile strain in the samples. Strain is defined as $l/l_0 \times 100\%$ where $l_0$ is the initial length of the sample array. This length is measured in the microscope and accurate to within 1%. The stage is mounted on the FTIR microscope in order to measure the resonance at each strain and each "relaxed" or deformed state. An SRR-bar coupled resonator geometry with w=800 nm, d=40 nm (FIG. 15—inset) and an initial resonant frequency of 5.78 μm (FIG. 15—blue line) is selected. The sample is stretched 25% parallel to the SRR arms, pulling the bar away from the SRR. When the strain is released, the PDMS between the resonators contracts causing the coupling distance to decrease from the initial value. The resonant wavelength is permanently red shifted to 6.27 μm, which is evident from the FTIR reflection spectrum (FIG. 15—dark red line). The new resonance coincides with the vibrational mode of interest in pMA at 1585 cm$^{-1}$, demonstrating how sensors with customizable responses can be designed with post-fabrication tunability.

The pMA is adsorbed to the surface of the PDMS in a manner similar to that used in microcontact printing. A drop of a 10 mM ethanolic solution of pMA is placed on the surface of the PDMS and allowed to dry. The sample is measured after drying and an obvious dip is present in the center of the resonant peak (FIG. 15—red line) which represents a ΔR of 0.9%. The cross-polarized data are also reported (red dashed line) and show that the molecular signal from the metamaterial substrate is due to the overlap of the metamaterial resonance and the pMA vibrational modes. The pMA signal was not apparent on bare patches of the PDMS or on arrays whose resonances did not overlap with the vibrational modes. It is assumed that a number of molecules, those adhered to the Au and those between the SRR and bar, contribute to the signal. An enhancement factor is not reported for the vibrational modes of pMA on PDMS-based resonators as it is unclear exactly how many molecules contribute to the signal and will depend on the diffusion of pMA through the PDMS. Nevertheless, the observed signal for the pMA coated sample is the first report of SEIRA from a compliant substrate and suggests that polymeric based metamaterials could be useful platforms for sensing given both their in situ tunability and the potential for integration with polymeric-based devices, such as microfluidic cells. The signal from these types of sensors could be increased by using higher index polymeric substrates (such as pMA), making this approach a promising step forward in the design of flexible, tunable metamaterial-based sensors.

It has been shown that compliant metamaterials can be used to sense changes in refractive index at a number of resonant frequencies with FOM values of up to 10.1. It has also been shown that resonator size can be used to tune the resonant frequency through the IR and achieve sensitivities of 3370 nm/RIU (120 meV/RIU) for large resonators at long wavelengths and 1190 nm/RIU (500 meV/RIU) for small resonators in the near IR. It has also been demonstrated that by coupling the metamaterial resonance to particular vibrational modes, enhancement of a vibrational mode signal with coupled Au resonators on Si by a factor of $10^4$ can be achieved. Resonators on a compliant substrate can be stretched and mechanically deformed in order to optimize the alignment of a vibrational mode with the metamaterial resonant frequency post-fabrication, and vibrational modes at frequencies more than a linewidth distance from the as-fabricated resonance could be accessed by inducing substrate strain. Exploiting and tailoring the mechanical deformation of these metamaterial systems opens the door to the possibility of creating a new class of in situ customizable sensing surfaces.

Using mechanical deformation of a compliant substrate to achieve an active response in metamaterial surfaces sets the stage for new types of metamaterial design. Metamaterials were previously restricted to hard, brittle substrates, but attaching patterns to an elastomeric substrate enables their use in flexible electronics and allows post-fabrication adjustments of their properties. In this application, it is shown how different shapes can affect the local mechanical properties of a device. For designs that experience high local strain, it was found that the deformation for low global strain is plastic and fixes the final resonance position. When the local strain is evenly distributed across a structure, the deformation is much more likely to be elastic in nature. Coupled resonator pairs were used to illustrate how the coupling constant affects the resonant frequency of a particular SRR design. Strongly coupled resonator pairs lead to improved tunability of the design, which is of particular importance in the design of metamaterial-based optical filters and modulators. It was also shown how these resonators could be used as metamaterial-based sensors and show that the absorption feature corresponding to the vibrational mode of the C—H stretch bond can be enhanced 225 times. An important feature of any active metamaterial is the elasticity of its response and here it has been shown how mechanical deformation can set new limits for elastic tunability.

Moreover, large strain mechanical deformation of a compliant metamaterial has been demonstrated to achieve resonant frequency tuning by up to a line width, and the mechanical control of coupled resonators has been shown to tunably enhance infrared absorption of a molecular vibrational mode, which could provide a new degree of freedom in molecular sensing and detection. These structures are highly compliant bendable, stretchable and tunable metamaterials, and signal a departure from the use of brittle, hard, inorganic materials to achieve complex optical material responses.

While the present invention has been illustrated and described with reference to certain exemplary embodiments, those of ordinary skill in the art will understand that various modifications and changes may be made to the described embodiments without departing from the spirit and scope of the preset invention, as defined in the following claims.

What is claimed is:
1. A tunable metamaterial structure, comprising:
a flexible substrate capable of being strained;
a metamaterial pattern on a surface of the flexible substrate; and
a metal layer on the metamaterial pattern;
wherein the flexible substrate is a strained and relaxed substrate which has been strained to a degree sufficient to register a resonant response upon relaxation that is shifted relative to a resonant response of the flexible substrate prior to being strained.

2. The tunable metamaterial structure of claim 1, wherein the strained and relaxed substrate has been strained to a degree of about 5% or greater.

3. The tunable metamaterial structure of claim 1, wherein the strained and relaxed substrate has been strained to a degree of about 10% or greater.

4. The tunable metamaterial structure of claim 1, wherein the strained and relaxed substrate has been strained to a degree of about 20% or greater.

5. The tunable metamaterial structure of claim 1, wherein the strained and relaxed substrate has been strained to a degree of up to about 100%.

6. The tunable metamaterial structure of claim 1, wherein the strained and relaxed substrate has been strained to a degree of about 5% to about 50%.

7. The tunable metamaterial structure of claim 1, wherein the strained and relaxed substrate has been strained to a degree of about 10% to about 50%.

8. The tunable metamaterial structure of claim 1, wherein the strained and relaxed substrate has been strained to a degree of about 20% to about 50%.

9. The tunable metamaterial structure of claim 1, wherein the flexible substrate comprises a material selected from the group consisting of flexible polymers, rubbers and vinyl acetates.

10. The tunable metamaterial structure of claim 1, wherein the flexible substrate comprises a material selected from the group consisting of polydimethylsiloxane (PDMS), polyimide, polybutadiene rubbers, and vinyl acetates.

11. The tunable metamaterial structure of claim 1, wherein the flexible substrate comprises polydimethylsiloxane (PDMS).

12. The tunable metamaterial structure of claim 1, wherein the metal layer comprises a metal selected from the group consisting of Au, Ag, Cu and Pt.

13. A tunable sensor, comprising the tunable metamaterial structure of claim 1.

14. The tunable sensor of claim 13, wherein the tunable metamaterial structure is capable of resonantly enhanced infrared absorption spectroscopy.

15. The tunable sensor of claim 13, wherein tunable metamaterial structure is capable of refractive index sensing.

16. The tunable sensor of claim 13, wherein the strained and relaxed substrate has been strained to a degree of about 20% or greater.

17. The tunable sensor of claim 13, wherein the metamaterial structure senses an analyte.

18. The tunable sensor of claim 13, wherein the analyte is p-mercaptoaniline.

19. A tunable sensor, comprising:
a tunable metamaterial structure that senses an analyte, comprising:
a flexible substrate capable of being strained;
a metamaterial pattern on a surface of the flexible substrate; and
a metal layer on the metamaterial pattern,
wherein the metamaterial structure enhances an infrared absorption signal of the analyte.

* * * * *